United States Patent
Swenson

(10) Patent No.: US 7,316,668 B2
(45) Date of Patent: Jan. 8, 2008

(54) NEEDLE SHIELD ASSEMBLY

(75) Inventor: Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 377 days.

(21) Appl. No.: 10/392,125

(22) Filed: Mar. 19, 2003

(65) Prior Publication Data
US 2003/0181873 A1 Sep. 25, 2003

Related U.S. Application Data

(60) Provisional application No. 60/365,921, filed on Mar. 20, 2002.

(51) Int. Cl.
*A61M 5/32* (2006.01)

(52) U.S. Cl. .................. 604/192; 604/198; 604/263

(58) Field of Classification Search ................ 604/110, 604/187, 192, 197, 198, 263
See application file for complete search history.

(56) References Cited

U.S. PATENT DOCUMENTS

| | | |
|---|---|---|
| 4,872,552 A | 10/1989 | Unger |
| 5,135,509 A | 8/1992 | Olliffe |
| 5,139,489 A | 8/1992 | Hollister |
| 5,188,611 A | 2/1993 | Orgain |
| 5,405,332 A | 4/1995 | Opalek |
| 5,423,765 A | 6/1995 | Hollister |
| 5,584,816 A | 12/1996 | Gyure et al. |
| 5,599,318 A | 2/1997 | Sweeney et al. |
| 5,649,622 A | 7/1997 | Hollister |
| 5,662,617 A | 9/1997 | Odell et al. |
| 5,746,726 A * | 5/1998 | Sweeney et al. ............ 604/263 |
| 5,891,103 A | 4/1999 | Burns |
| 5,957,892 A | 9/1999 | Thorne |
| 6,015,397 A | 1/2000 | Elson et al. |
| 6,036,675 A | 3/2000 | Thorne et al. |
| D422,700 S | 4/2000 | Crawford et al. |
| 6,120,482 A * | 9/2000 | Szabo ........................ 604/192 |
| RE37,110 E | 3/2001 | Hollister |
| 6,221,058 B1 | 4/2001 | Kao et al. |
| D442,280 S | 5/2001 | Crawford et al. |
| RE37,252 E | 7/2001 | Hollister |
| 6,298,541 B1 * | 10/2001 | Newby et al. ................ 29/458 |
| 6,582,397 B2 * | 6/2003 | Alesi et al. .................. 604/110 |
| 2001/0008963 A1 | 7/2001 | Alesi |
| 2001/0039401 A1 | 11/2001 | Ferguson et al. |

OTHER PUBLICATIONS

"Compact Oxford English Dictionary"—definition of "flange" http://www.askoxford.com/concise_oed/flange?=view=uk.*

* cited by examiner

*Primary Examiner*—Kevin C. Sirmons
*Assistant Examiner*—Catherine N. Witczak
(74) *Attorney, Agent, or Firm*—Mark Lindsey

(57) ABSTRACT

A safety needle assembly including a needle with an intravenous puncture tip, a shield in pivotal engagement with respect to the needle, and a hub in the form of a collar providing pivotal engagement between the needle and the shield is provided. The shield is pivotally movable between an unshielded position and a shielded position in which a portion of the shield encompasses the intravenous puncture tip for shielding the needle for safety purposes. The collar and the shield include locking structure providing locking engagement therebetween for locking the shield in the shielded position for preventing pivotal movement to the unshielded position. The collar further includes at least one collar flange extending laterally along a portion of the collar for preventing disengagement of the locking structure.

8 Claims, 38 Drawing Sheets

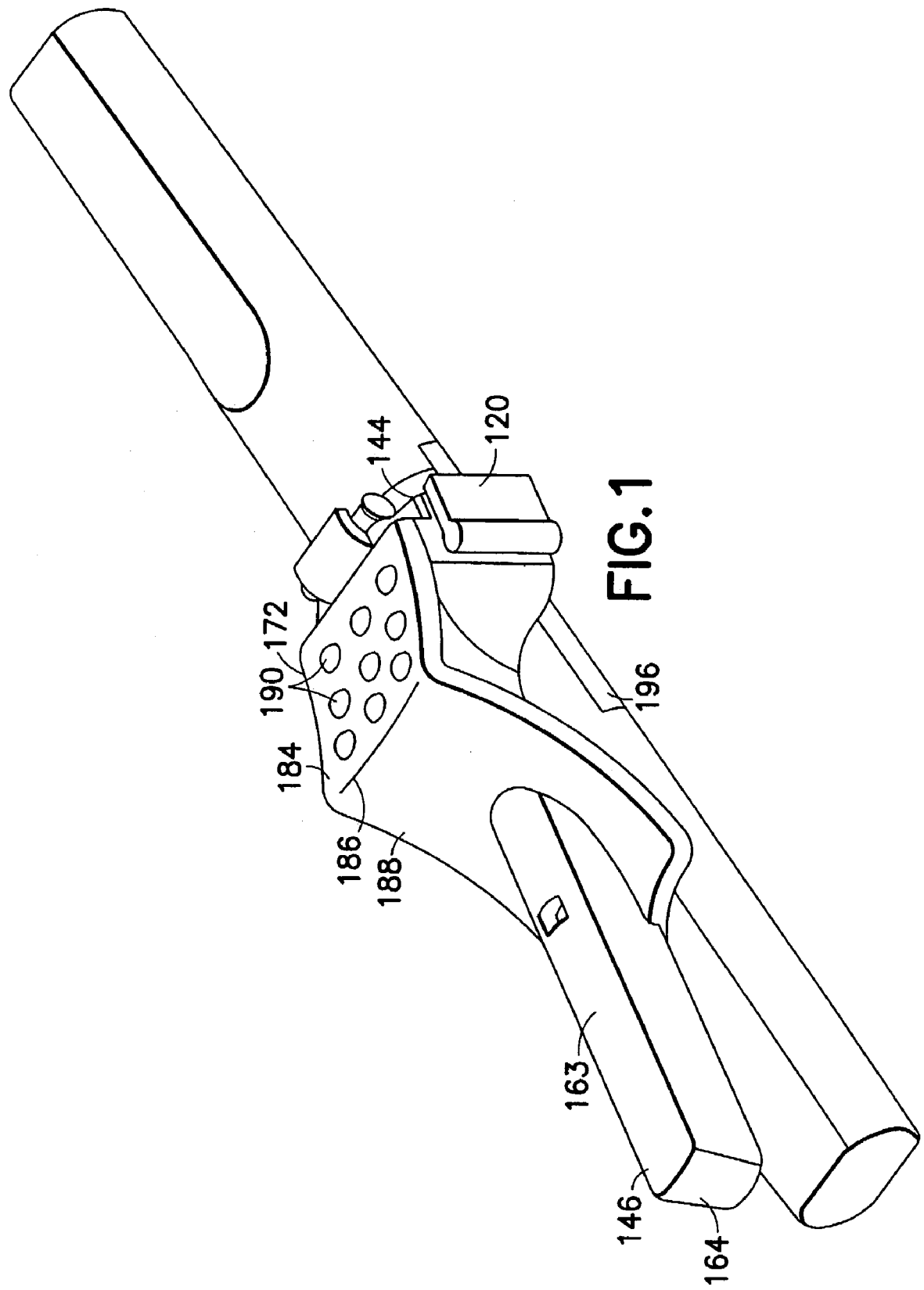

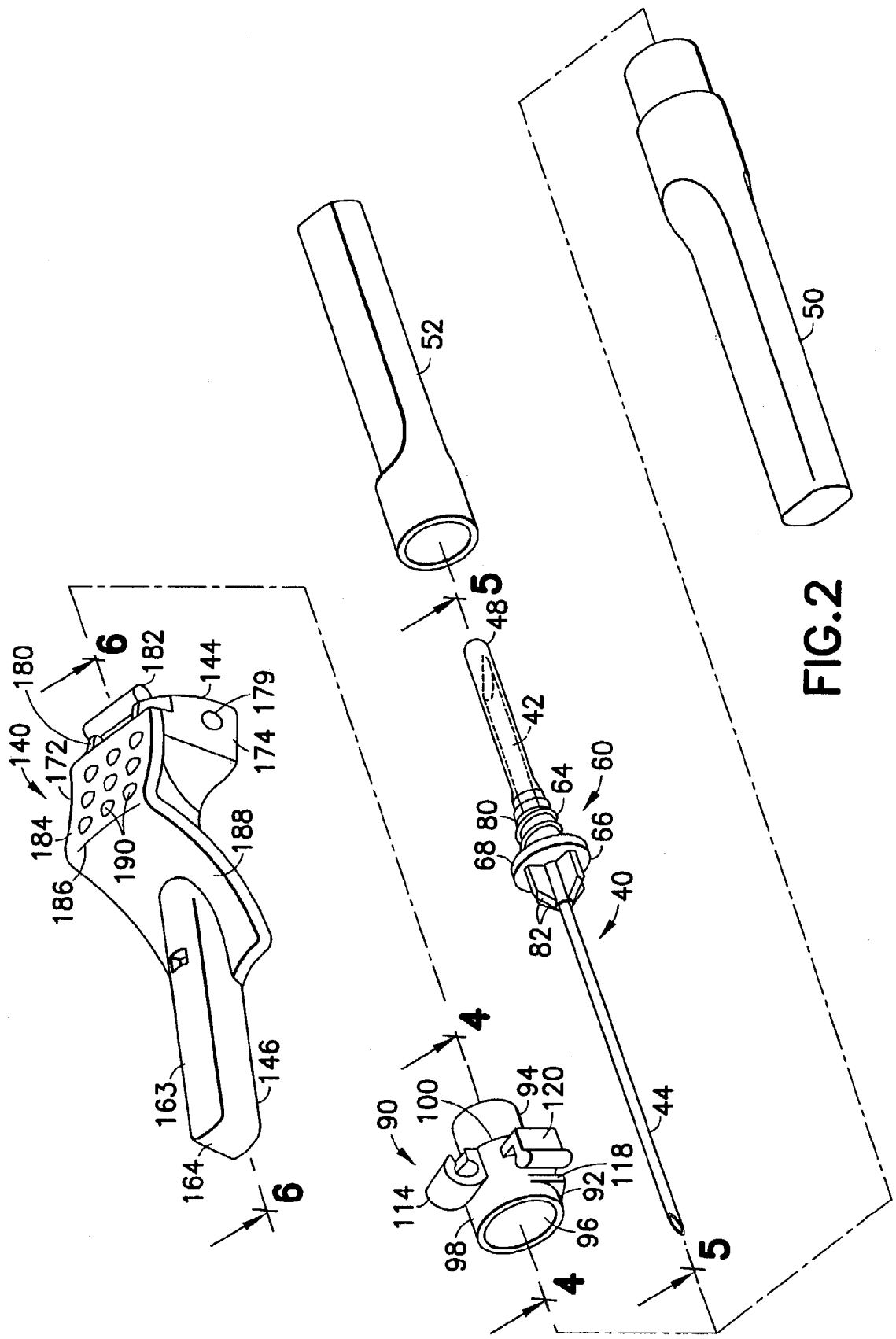

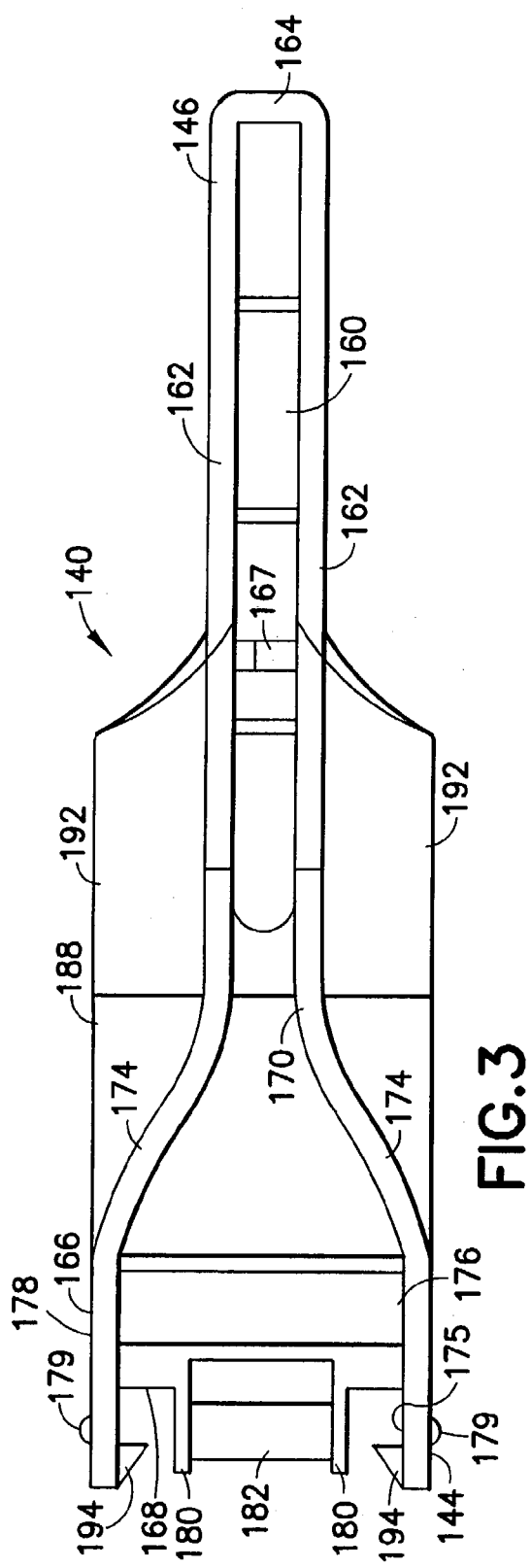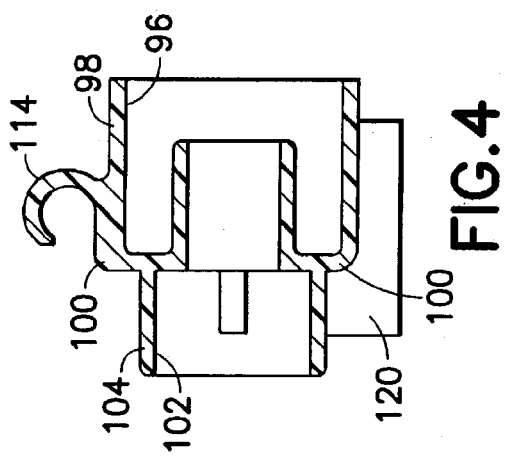

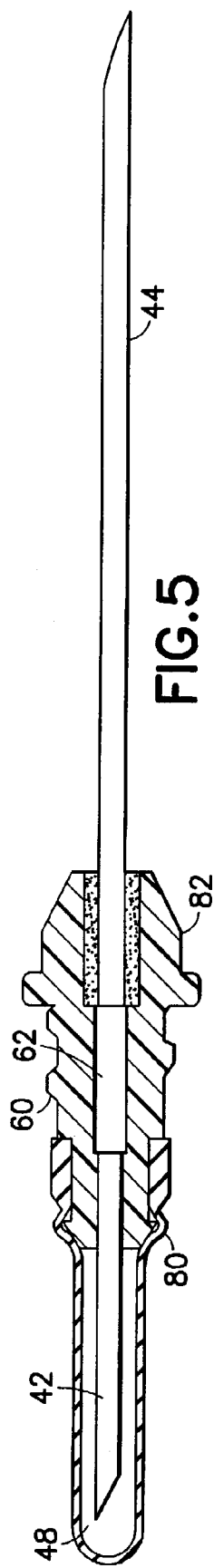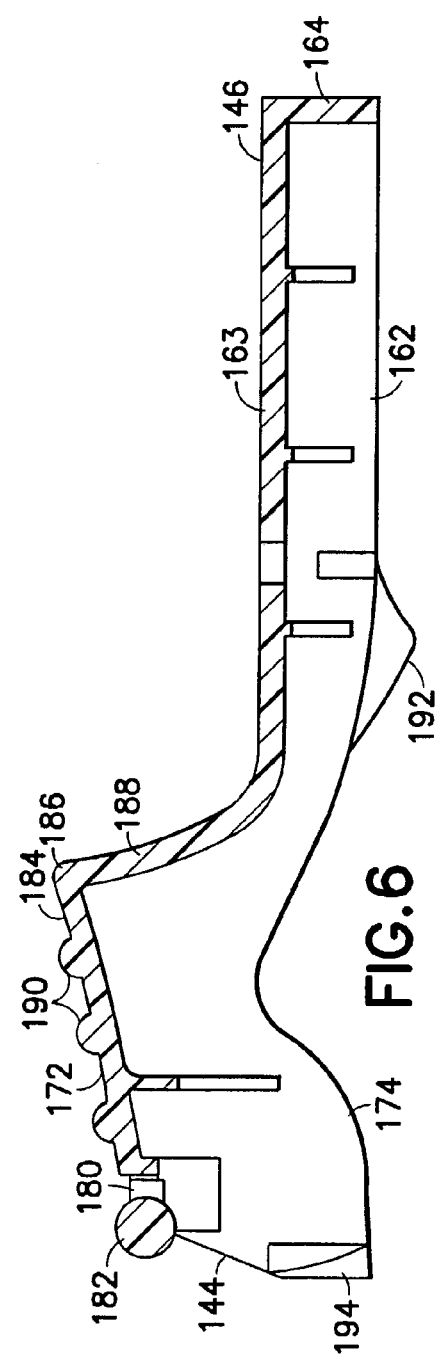

NEEDLE SHIELD ASSEMBLY

CROSS-REFERENCE TO RELATED APPLICATIONS

This application claims the benefit of U.S. Provisional Application No. 60/365,921 filed Mar. 20, 2002.

BACKGROUND OF THE INVENTION

1. Field of the Invention

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handling devices or assemblies that contain piercing elements.

2. Description of Related Art

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannulae or blunt ended cannulae.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies.

For example, a number of devices incorporate a pivoting shield assembly in which the shield can be pivoted away from the needle during use and pivoted about the needle after use, for protection from the used needle. U.S. Pat. No. 5,188,611 discloses a reusable safety needle arrangement having a collar for engaging a needle and a slotted longitudinal shield which is attached to the collar at a hinge for pivoting over the needle. The arrangement includes a locking mechanism for locking the shield over the needle, which locking mechanism is provided through a set of flanges on the shield which grip a set of complementary catches on the collar. Such an arrangement is specifically designed to be reusable, such that the locking member can be reversed by pinching the shield to cause the flanges and catches to disengage to release the shield from the collar. Such an arrangement with a reversible locking mechanism potentially exposes a user to a used needle tip, in that the shield can be retracted from the needle after the needle has been used and shielded.

Various mechanisms for locking the shield in place over the needle by direct engagement with the needle have also been developed to prevent re-exposure of the needle. For example, the U.S. Pat. No. 5,188,611 patent further discloses a keeper within the slot of the longitudinal shield, which engages directly with the needle cannula as a locking mechanism. Such a keeper is disclosed as being reversible through manipulation of the mechanism. Further, locking engagement directly with the needle may cause the needle to vibrate, thereby increasing the chances of blood spatter from the needle tip.

In view of the foregoing, a need exists for a shieldable needle assembly that achieves secure and effective irreversible shielding of a used needle cannula which is simple and inexpensive to manufacture and easy to operate.

SUMMARY OF THE INVENTION

The present invention is directed to a shieldable safety assembly, and in particular, to a safety needle assembly. The safety needle assembly includes a needle cannula with an intravenous end having a puncture tip, a shield in pivotal engagement with respect to the needle cannula, and a hub in the form of a collar providing pivotal engagement between the needle cannula and the shield. The shield is pivotally movable between a retracted or unshielded position in which the shield is pivotally spaced from the intravenous end of the needle cannula, and a shielded position in which a portion of the shield encompasses the intravenous end of the needle cannula, thereby shielding the needle for safety purposes. The collar and the shield include structure for locking engagement therebetween for locking the shield in the shielded position for preventing pivotal movement to the unshielded position. The collar further includes at least one collar flange extending laterally along a portion of the collar for preventing disengagement of the locking structure.

The shield includes a pair of longitudinally extending sidewalls defining a longitudinal opening for containing the needle cannula when the shield is pivotally rotated to the shielded position. The shield may include an outer shield flange on at least one, and preferably both sidewalls, with the outer shield flanges and the sidewalls forming openings for receiving the collar flanges. Inner shield flanges may further be provided on the sidewalls, and the outer shield flanges and inner shield flanges may be connected at the bottom ends.

At least one, and preferably both of the sidewalls, of the shield include locking structure for engaging with the collar when the shield is in the shielded position. The locking structure may be provided through locking barbs at a rearward end of the sidewalls for interengagement with corresponding locking dents on the collar, such that the locking barbs and locking dents are interengagable when the shield is in the shielded position. Alternatively or in addition to the locking barbs and locking dents, the engagement between the collar flanges and the outer shield flanges may provide locking structure between the shield and the collar.

The collar flanges may include an outer latch for engagement with the outer shield flanges, and may further include an inner latch for engagement with inner shield flanges on the outer surfaces of the sidewalls. In addition, the collar includes structure for mating with a medical device, such as a threaded end for attachment to a conventional needle holder or a luer fitting for attachment to a syringe. Preferably, the needle cannula includes a non-patient end extending from a rearward end of the collar and an intravenous end extending from a forward end of the collar.

In a further embodiment, the present invention is directed to a safety assembly including a needle assembly and a needle shield assembly. The needle assembly includes a hub and a needle connected to the hub, with a non-patient end and an intravenous end with a puncture tip. The needle shield assembly is connected to the needle assembly and includes a collar and a shield. The collar is connected to the hub of the needle assembly and the shield is movably connected to the collar such that the shield may be pivoted with respect to the collar between a retracted position in which the shield is pivotally spaced from the intravenous end of the needle and a shielded position in which the shield encompasses the intravenous end of the needle. The collar and the shield include locking structure for locking engagement therebetween, and the collar further includes a collar flange extending laterally along a portion of the collar. When the shield is in the shielded position, the locking structure is engaged, and the collar flange prevents the locking structure from being disengaged.

The shield and the collar may be connected through an interference fit between a hanger bar located on the shield and a hook arm located on the collar, providing for pivotal engagement of the shield between the retracted position and the shielded position. The collar may include a forward annular skirt having an inner surface and an outer surface and a rearward annular skirt having an inner surface and an outer surface. The collar flange preferably extends laterally from the outer surface of the rearward annular skirt in a direction toward the forward annular skirt.

In yet a further embodiment, the invention is directed to a safety assembly which includes a needle assembly and a needle shield assembly as described, as well as a needle holder connected to a rearward end of the collar and with a non-patient end of the needle assembly extending within the needle holder.

DESCRIPTION OF THE DRAWINGS

FIG. 1 is a perspective view of the safety shield assembly of the present invention as connected to a needle assembly and related packaging features;

FIG. 2 is a perspective view of the unassembled pieces of FIG. 1;

FIG. 3 is a bottom view of the shield as shown in FIG. 2;

FIG. 4 is a cross sectional view of the collar as shown in FIG. 2 taken along lines 4-4 thereof;

FIG. 5 is a cross sectional view of the needle hub as shown in FIG. 2 taken along lines 5-5 thereof;

FIG. 6 is a cross sectional view of the shield as shown in FIG. 2 taken along lines 6-6 thereof;

DETAILED DESCRIPTION

Figure 7:
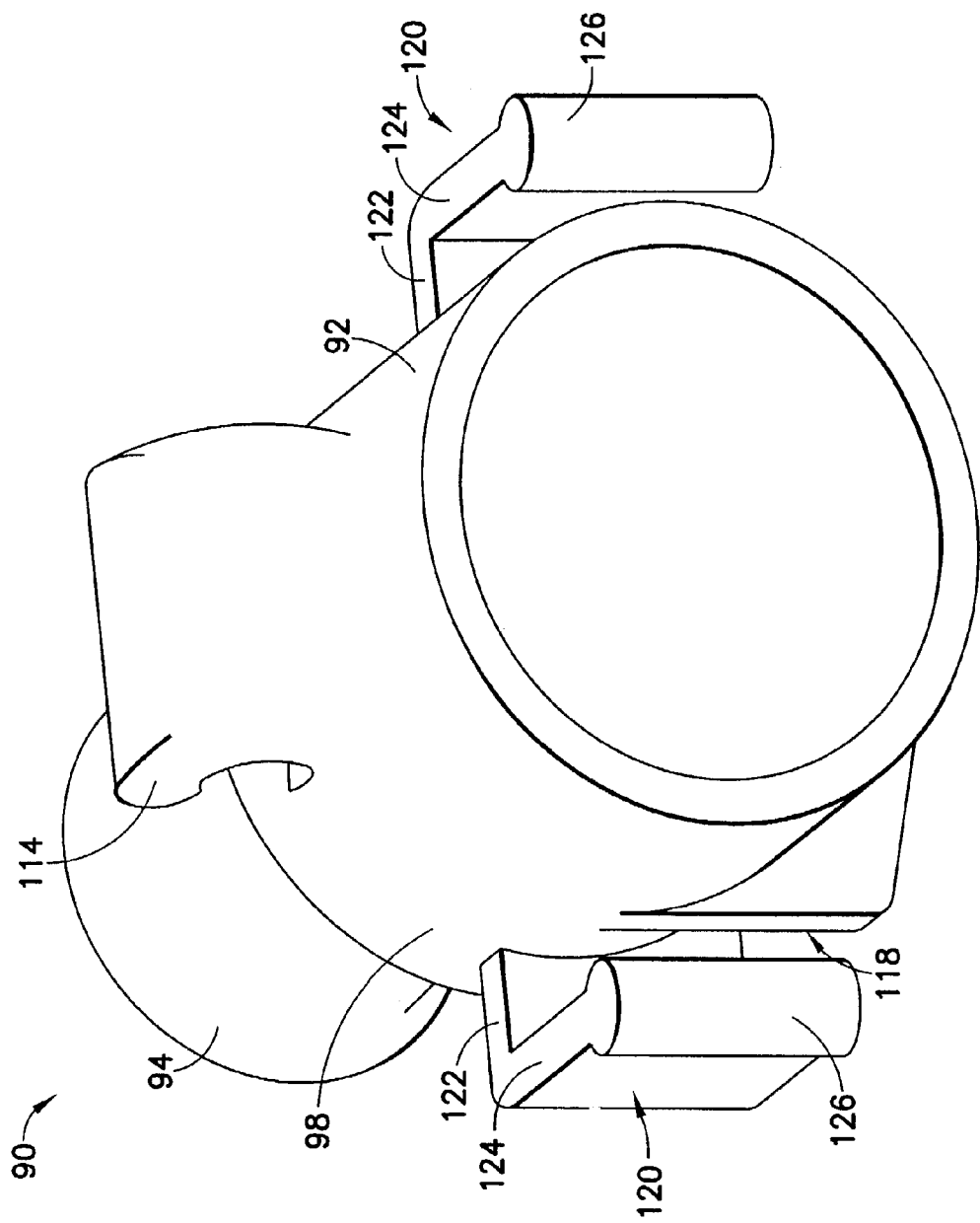
FIGS. 7 and 8 are top and bottom perspective views of the collar as shown in FIG. 2.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 and 2 illustrate a needle assembly with the safety shield assembly of the present invention and the related packaging features. The needle assembly includes a needle 40 and a hub 60, with packaging features to cover the needle as well as a label. The safety shield assembly includes a collar 90 and a shield 140.

As shown in FIGS. 2 and 5, needle 40 includes a non-patient end 42, an intravenous end 44 and a passageway 46 extending between non-patient end 42 and the intravenous end 44. An elastomeric sleeve 48 covers the non-patient end, a rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between threaded end 64 and ribbed end 66. Threaded end 64 and ribbed end 66 are separated by flange 68. Non-patient end 42 of needle 40 extends from threaded end 64, and intravenous end 44 of needle 40 extends from ribbed end 66. Preferably, threaded end 64 comprises male threads 80 for mounting hub 60 on a conventional needle holder and ribbed end 66 comprises male ribs 82 for connecting the hub 60 and collar 90.

As shown in FIGS. 2, 4, 7 and 8, collar 90 includes two sections, a forward annular skirt 92 and a rearward annular skirt 94. The forward annular skirt is cylindrical comprising an inner sidewall 96 and an outer sidewall 98 and mates with the rearward annular skirt at a shoulder 100. Rearward annular skirt 94 is cylindrical comprising an inner sidewall 102 and an outer sidewall 104 and extends from shoulder 100 opposite of forward annular skirt 92. The inner diameter of forward annular skirt 92 is larger than the inner diameter of rearward annular skirt 94. Alternatively, the inner diameters for collar 90 can be formed as a constant inner diameter.

Extending on outer sidewall 98 of forward skirt section 92 is a hook member 114, and located opposite or downwardly of hook member 114 on outer sidewall 98 are locking dents or protrusions 118.

Figure 8:
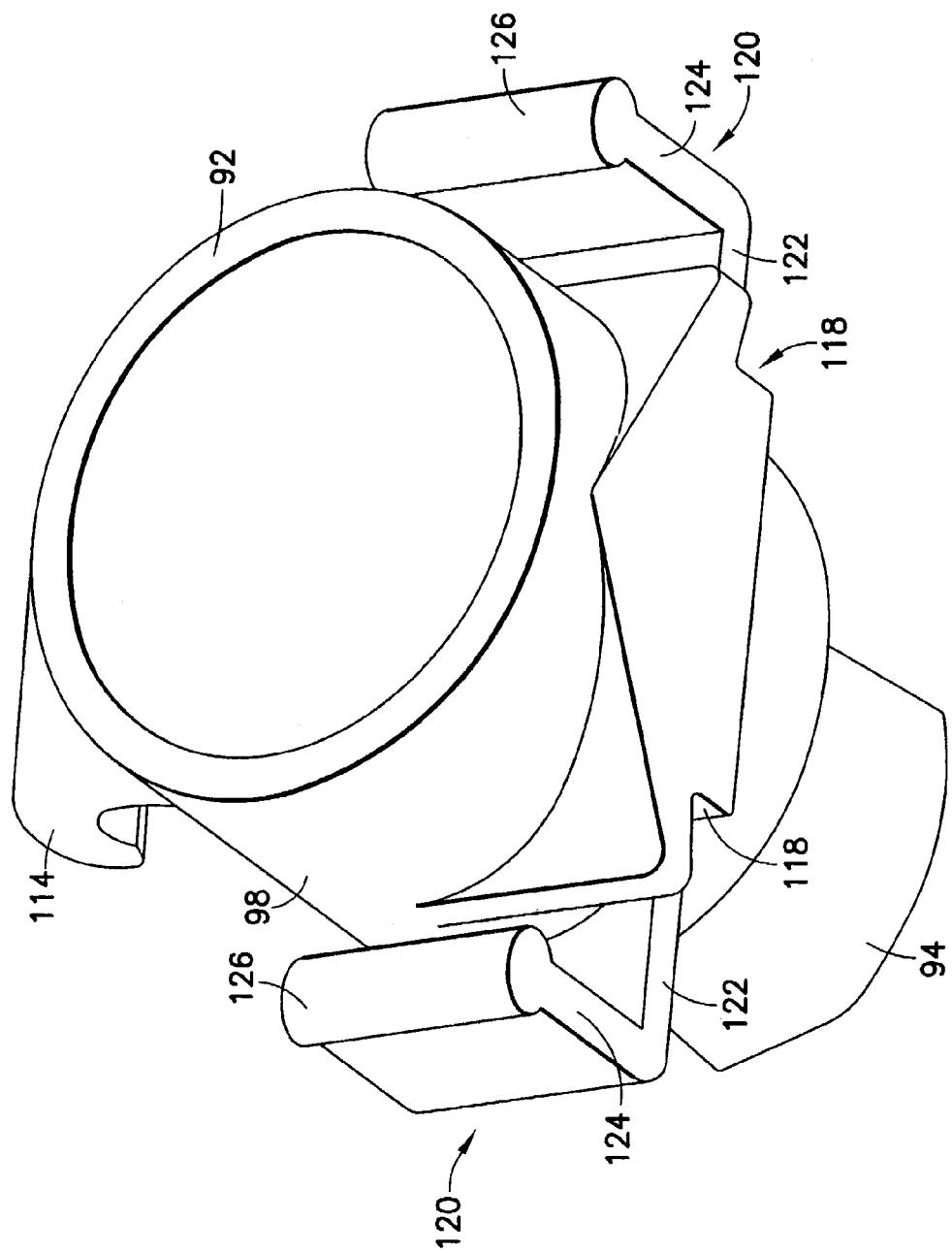
Figure 9:
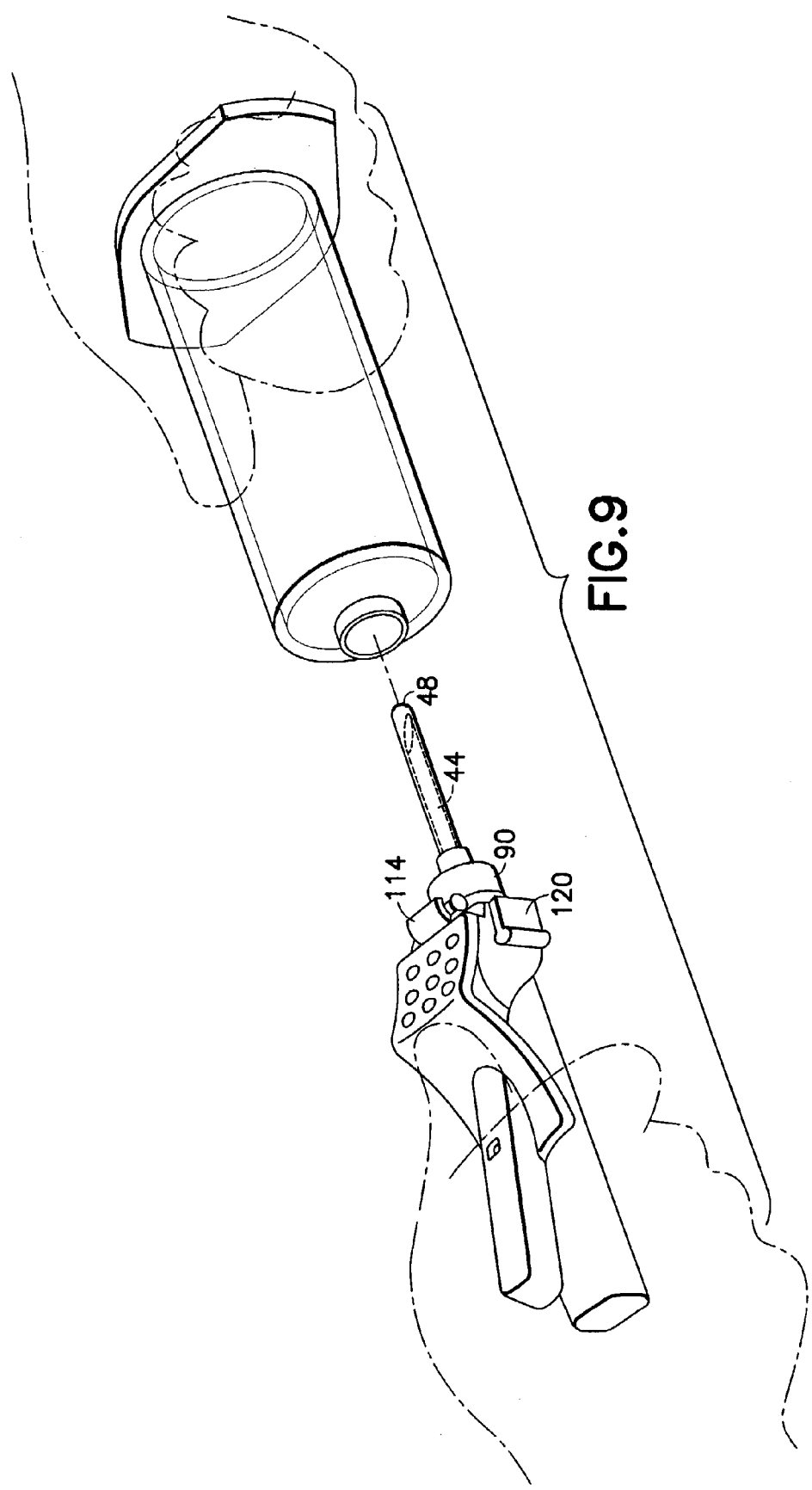
FIGS. 9-13 illustrate the use of the safety shield assembly with the needle assembly of FIG. 1 with a conventional needle holder.
Figure 10:
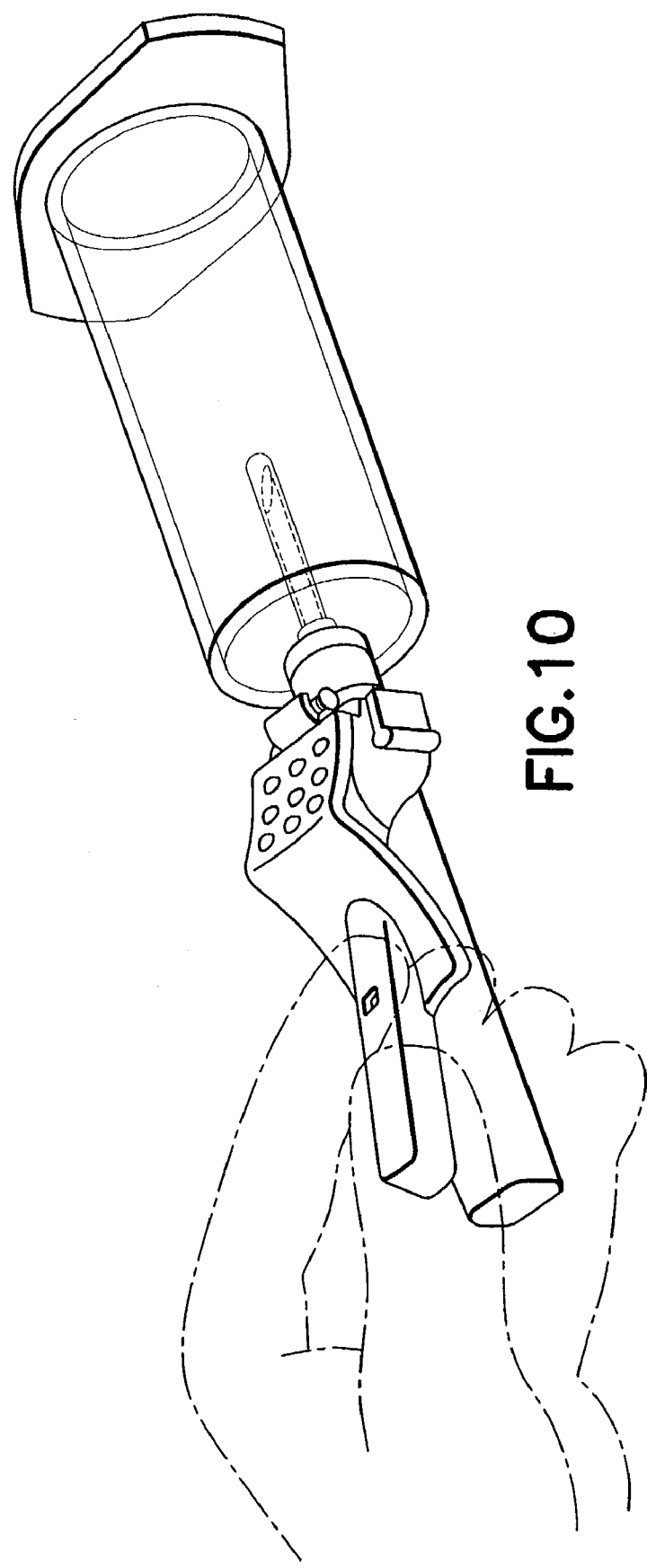

As seen clearly in FIGS. 7 and 8, collar 90 includes at least one collar flange 120 extending laterally along a portion of collar 90. Preferably, collar 90 includes a pair of collar flanges 120 extending laterally from opposing sides of collar 90 at forward annular skirt 92. In particular, collar flanges 120 extend from forward annular skirt 92 through a laterally extending portion 122, which turns at a shoulder to form a forward extending portion 124. The forward edge of collar flange 120 may be provided as a rounded forward edge 126, to assist in movement and engagement with shield 140, as will be discussed in more detail herein.

Collar flanges 120 extend laterally outwardly from collar 90 in a forward direction along forward annular skirt 92 at a position laterally adjacent locking dents or protrusions 118. In particular, as seen clearly in FIG. 8, forward extending portions 124 of collar flanges 120 extend along a portion of collar 90 at annular skirt 92 to protectively surround locking dents or protrusions 118. As will be discussed in more detail herein, collar flanges 120 prevent disengagement of a locking mechanism which is provided between shield 140 and collar 90 through locking dents or protrusions 118.

As shown in FIGS. 2, 3 and 6, shield 140 comprises a rearward end 144 and a forward end 146. Forward end 146 of shield 140 includes a slot or longitudinal opening 160 formed by sidewalls 162 that extend downwardly from top section 163 and run substantially opposite of one another in parallel along the length of slot 160 toward forward end sidewall 164. Means for trapping a needle in slot 160 may be provided in the form of an arm 167 that is located at one of sidewalls 162 to secure the used needle.

Arm 167 is deflectable by needle 40 when the needle 40 enters slot 160. Once needle 40 passes the end of arm 167, arm 167 moves back to its original position, whereby needle 40 is permanently trapped in slot 160 by arm 167.

At rearward end 144 of shield 140 is a collar engaging area 166 that is a continuation of slot 160. Collar engaging area 166 includes a rearward end 168, a forward end 170, a top finger guide area 172, parallel sidewalls 174 that extend downwardly and inwardly from top finger guide area 172 and into sidewalls 162, an underside area 176 for surrounding collar 90, and extending arms 180 to hold hanger bar 182. Parallel sidewalls 174 include an inner surface 175 where barb dents 194 are located. Parallel sidewalls 174 further include an outer surface 178, which may further include ribs 179 for interference engagement with the rounded forward edge 126 of collar flange 120 during pivotal rotation of shield 140 to the shielded position. Such an interference engagement provides a tactile indication that shield 140 has been pivotally rotated to the fully shielded position.

Top finger guide area 172 comprises a first ramp 184 that extends slightly on an upward slope from the rearward end of collar 90 engaging area to a shoulder 186. From shoulder 186 extends a second ramp 188 which slopes downwardly toward top section 163. Most preferably, first ramp 184 comprises touch bumps 190. Touch bumps 190 provide a tactile and visual guide to alert the user that the user's finger has contacted shield 90 and that the shield is in a defined or controlled position. Touch bumps 190 may be any configuration so long as they extend and are distinct from top finger guide area 172. Touch bumps 190 may also be of a distinguishing color as compared to top finger guide area 172 or shield 140.

Second ramp 188 has interior surface 192 for urging needle 40 toward the center of slot 160 as shield 140 is being rotated into the closed position. The exterior surfaces are slightly inclined and extending radially from second ramp 188. The interior surfaces are especially helpful if the longitudinal axis of needle 40 is misaligned with respect to the longitudinal axis of hub 60.

Figure 14:
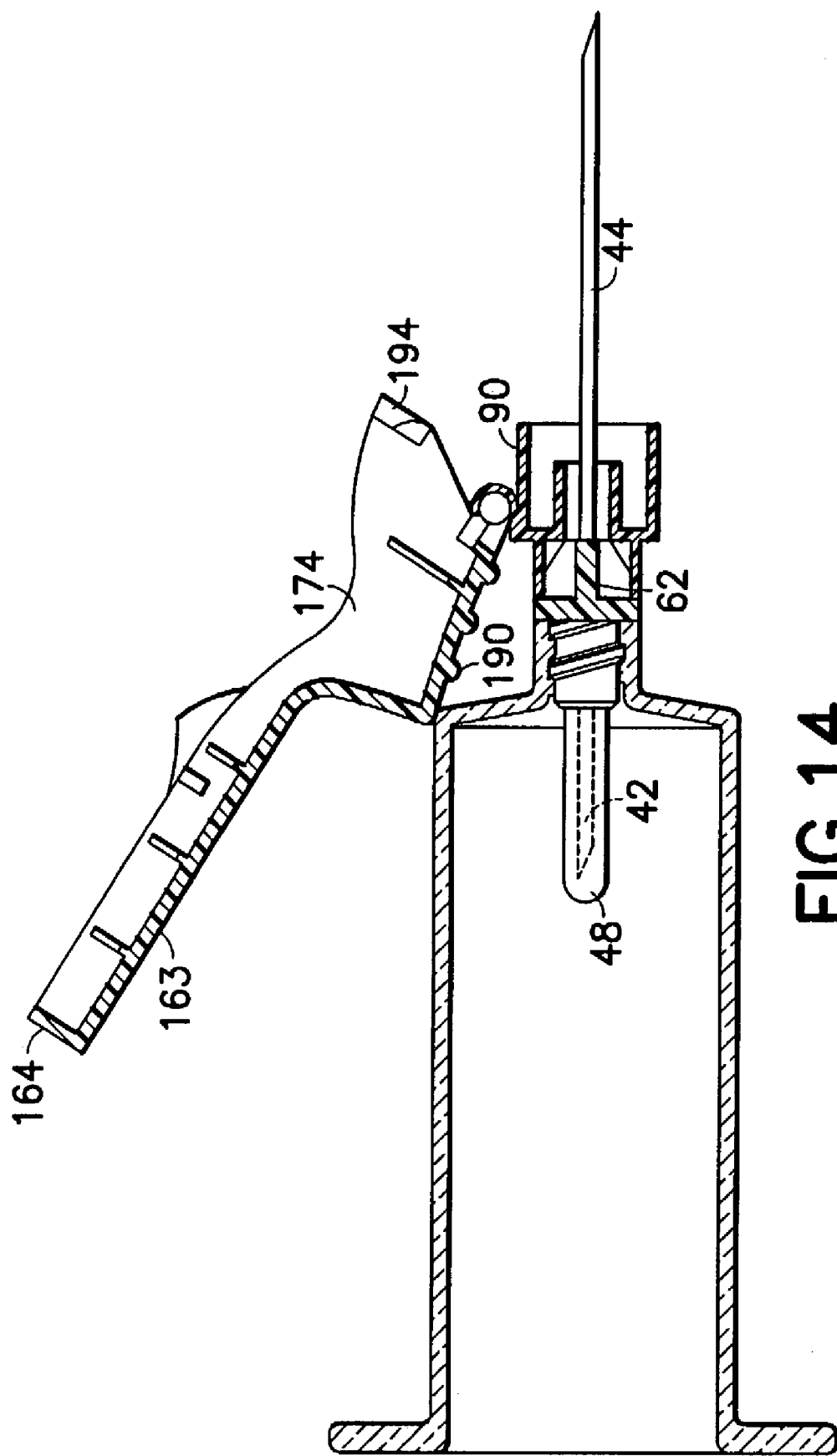
FIG. 14 is a cross sectional view of the assembly in use with a conventional needle holder with the shield in the retracted position as shown in FIG. 12.
Figure 15:
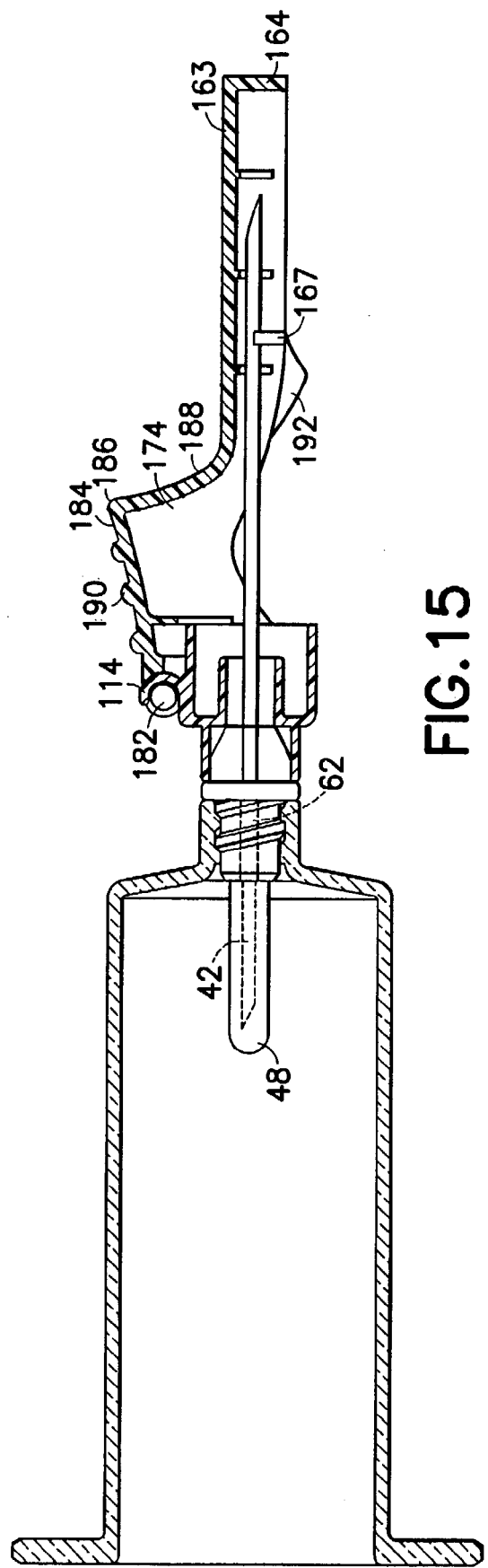
FIG. 15 is a cross sectional view of the assembly in use with a conventional needle holder with the shield in the shielded position as shown in FIG. 13.

Extending arms 180 are located at rearward end 168 and at the beginning of top finger area 172 and hold hanger bar 182. Hanger bar 182 is provided for pivotal engagement with hook member 114 of collar 90. Accordingly, the cooperating surfaces of hanger bar 182 and hook member 114 are designed so as to permit rotational or pivotal movement of shield 140 with respect to collar 90. Such engagement between hanger bar 182 and hook member 114 provides for pivotal movement of shield 140 between a retracted or unshielded position as shown in FIG. 14, with shield 140 pivotally spaced from intravenous end 44 of needle 40, and a shielded position as shown in FIG. 15, with shield 140 encompassing intravenous end 44 of needle 40.

Located downwardly from extending arm 180 and hanger bar 182 and on inner surface 175 of parallel sidewalls 174 are barb dents 194. Barb dents 194 cooperate with locking dents 118 on collar 90 to secure shield 140 in its final locked or shielded position.

The safety shield assembly and the needle assembly are assembled together whereby needle 40 is connected to hub 60 and sealed with adhesive at the ends of hub 60. Hub 60 is then joined with collar 90 by ultra-sonic welding techniques or any other bonding techniques, or mechanical fit, whereby rearward annular skirt 94 of collar 90 mates with ribbed end 66 of hub 60. Male ribs 82 of hub 60 are contained or force fitted within inner sidewall 102 of rearward annular skirt 94 of collar 90. Collar 90 is aligned with intravenous end 44 of needle 40 whereby the hook arm is aligned with the bevel tip of needle 40. Then rigid sleeve 50 is force fitted into inner sidewall 96 of forward annular skirt 92 of collar 90 to cover needle 40. Thereafter, shield 140 is connected to collar 90 whereby hanger bar 182 is force fitted into hook member 114 whereby slot 160 faces rigid sleeve 50. Most preferably, shield 140 is connected to collar 90 by a force fit or interface fit between hanger bar 82 and hook member 114. Therefore, shield 140 is always oriented in a stable position and will not move unless movement of the shield 140 is positively initiated by the user. To assemble the last piece, shield 140 is moved toward rigid sleeve 50 and second rigid sleeve 52 is force fitted onto outer sidewall 104 of rearward annular skirt 94 of collar 90.

In addition, a label 196 may be applied to the finally assembled parts. The label 196 may be used to prevent tampering of the parts, so that they are not reused.

Figure 11:
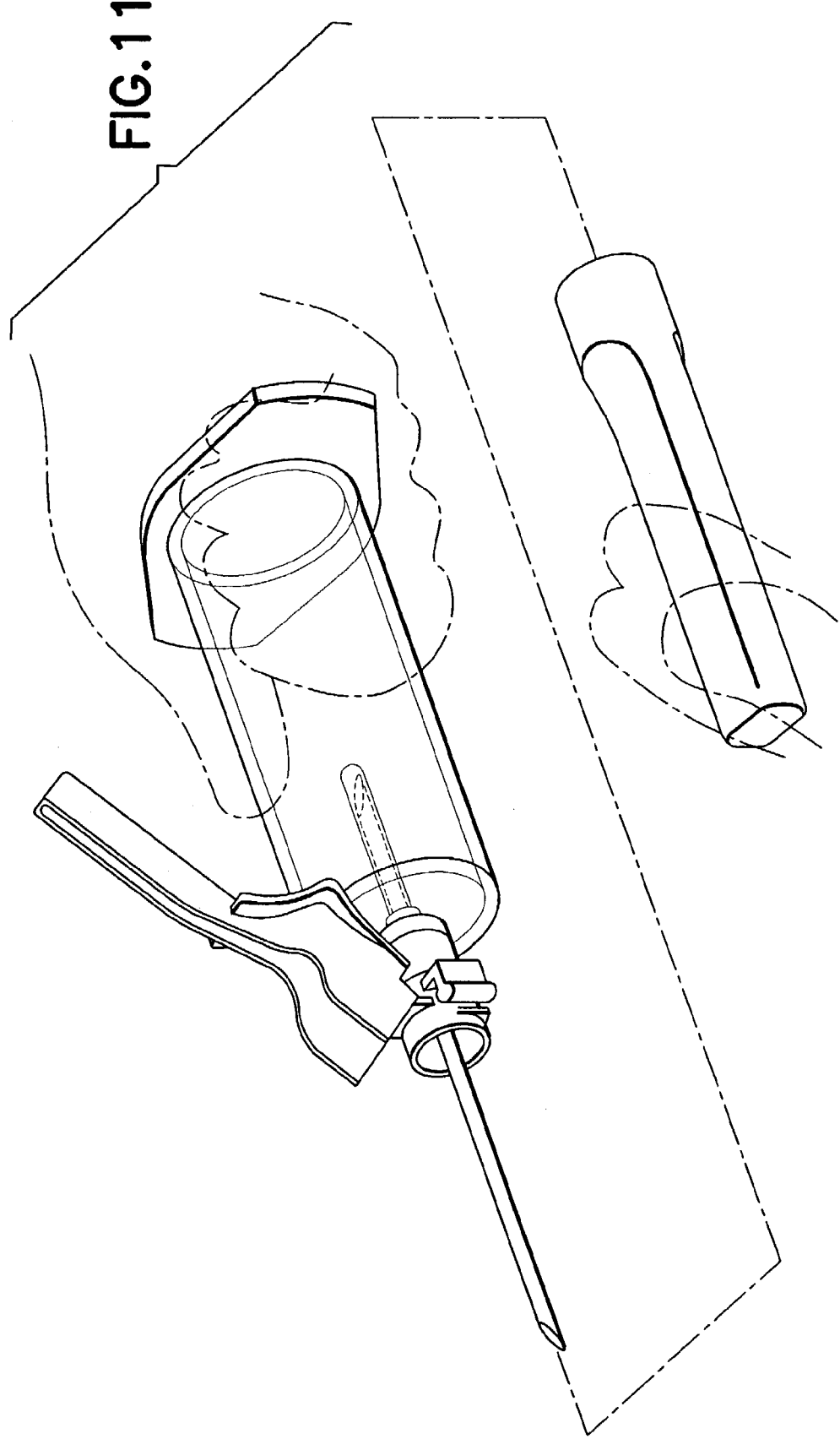
Figure 12:
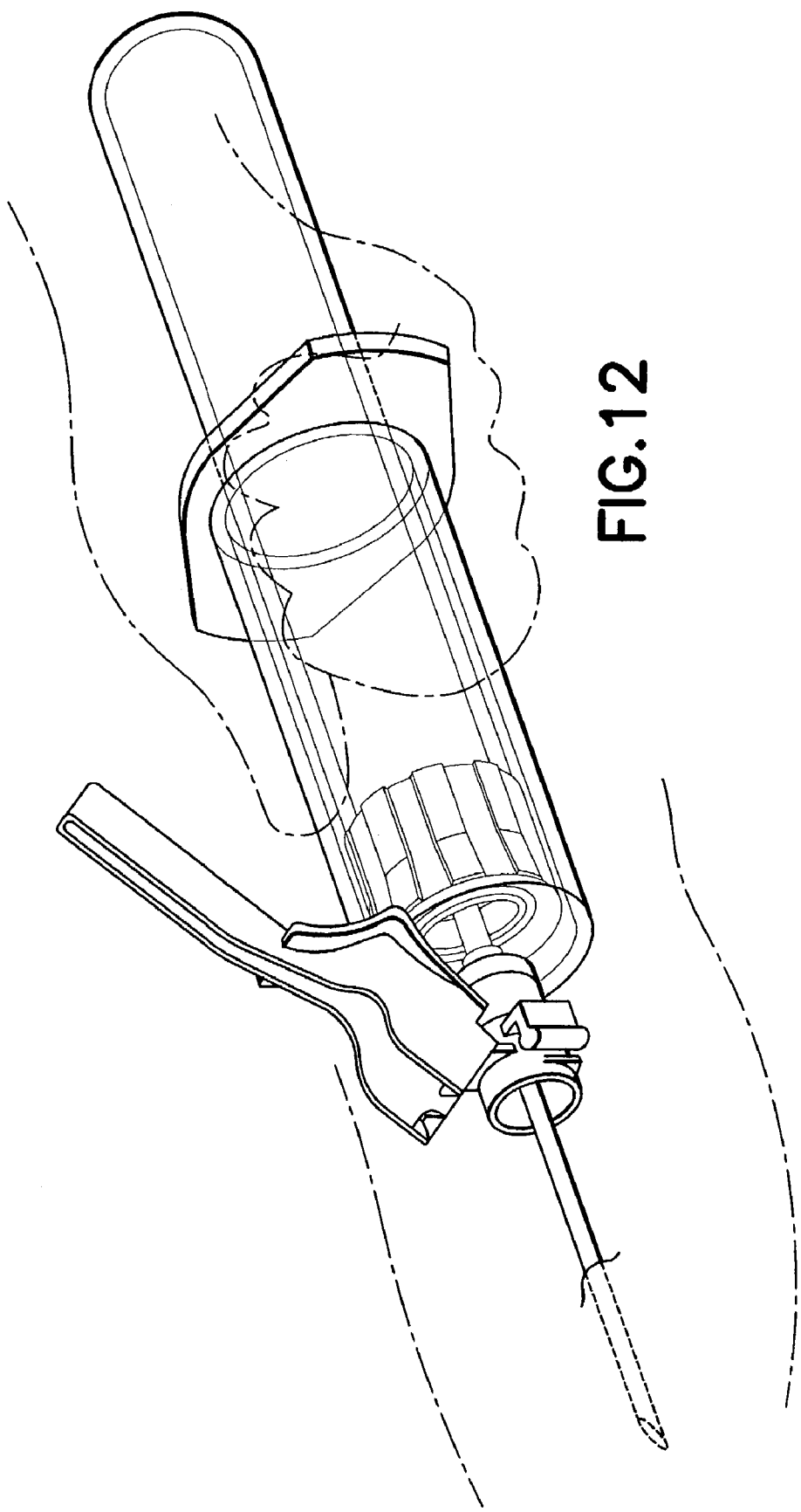
Figure 13:
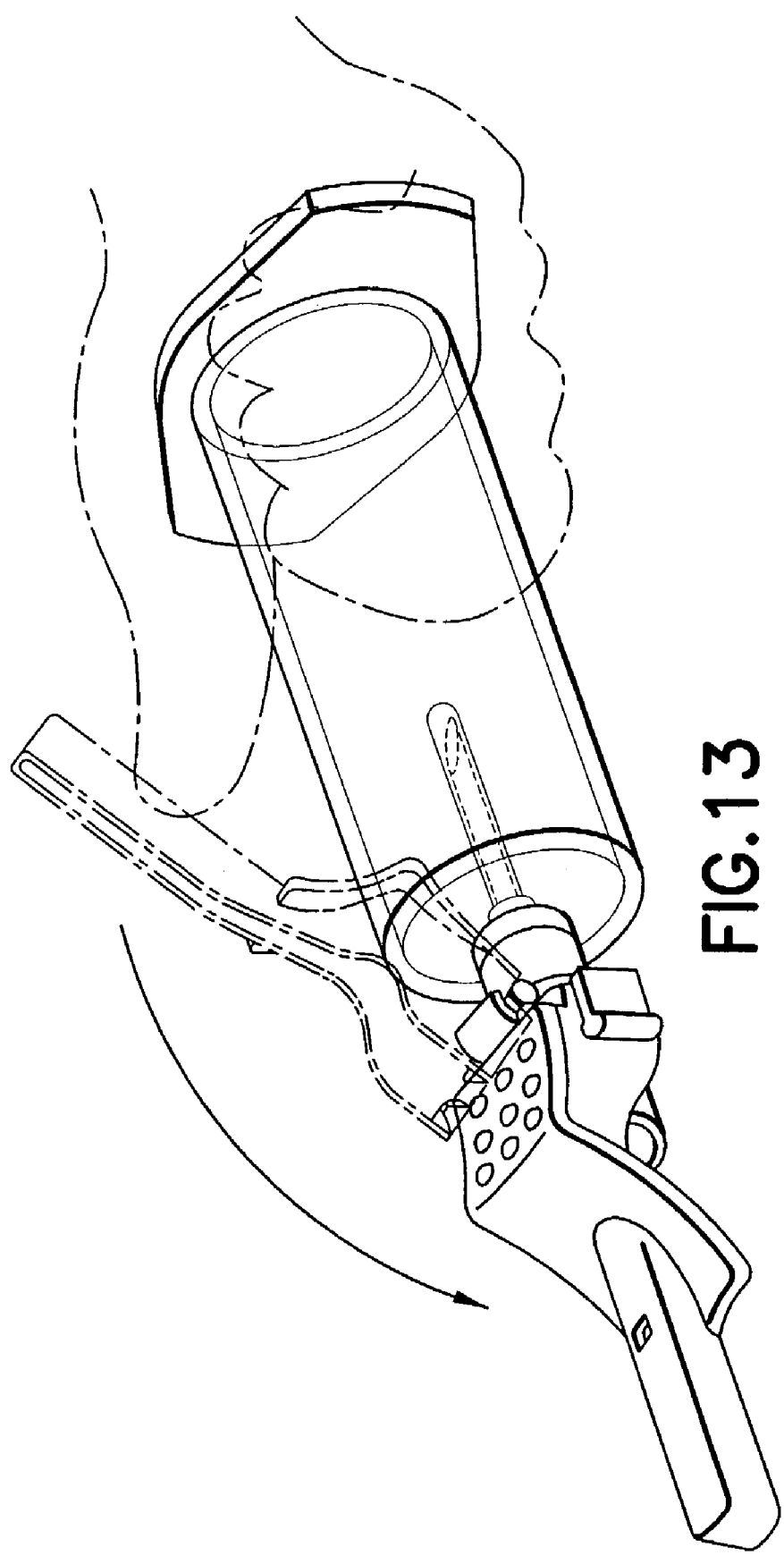

In use, as shown in FIGS. 9-16, non-patient needle shield 140 is removed and then a conventional needle holder is screwed onto hub 60 of needle 40. As specifically shown in FIGS. 10 and 14, shield 140 is then rotated back by user toward the needle holder. Then as shown in FIG. 11, intravenous needle shield 140 is removed from covering the intravenous needle. Then as shown in FIG. 12, a venipuncture is conducted whereby intravenous end 44 of the needle 40 is inserted into a vein of a patient and an evacuated tube having a closure is inserted into the needle holder. As shown in FIGS. 12 and 15, when the venipuncture is complete, the user easily pivotally rotates shield 140 from the open or unshielded position toward intravenous needle 40 to an intermediate position and then the user pushes on shield 140 at the top finger guide area to move shield 140 into a final, non-retractable shielded position whereby needle 40 is trapped in longitudinal opening 160.

During pivotal rotation of shield 140 to the shielded position, parallel sidewalls 174 at rearward end 144 of shield 140 rotate within the opening present between collar flange 120 and outer sidewall 198 of forward annular skirt 92 of collar 90. As shield 140 is pivoted, the rounded forward edges 126 of collar flange 120 pass over ribs 179 on outer surface 178 of parallel sidewalls 174, establishing an interference engagement which provides a tactile feel to the user that shield 140 has been rotated to the shielded position. In addition, barb dents 194 on inner surface 175 of parallel sidewalls 174 of shield 140 deflect over and are held by locking dents 118 of collar 90. The interengagement between barb dents 194 and locking dents 118 provides a locking structure for locking engagement between shield 140 and collar 90, thereby locking shield 140 in the shielded position and preventing pivotal rotation of shield 140 to the open or retracted position. Collar flanges 120 laterally extending from opposing sides of outer sidewall 98 and extending along the lateral sides of the forward annular skirt 92 prevent parallel sidewalls 174 of shield 140 from being extended or flexed outwardly to disengage barb dents 194 from locking dents 118. Accordingly, collar flanges 120 prevent disengagement of the locking structure, thereby ensuring that shield 140 remains in the shielded position preventing any exposure of needle 40.

Figure 16:
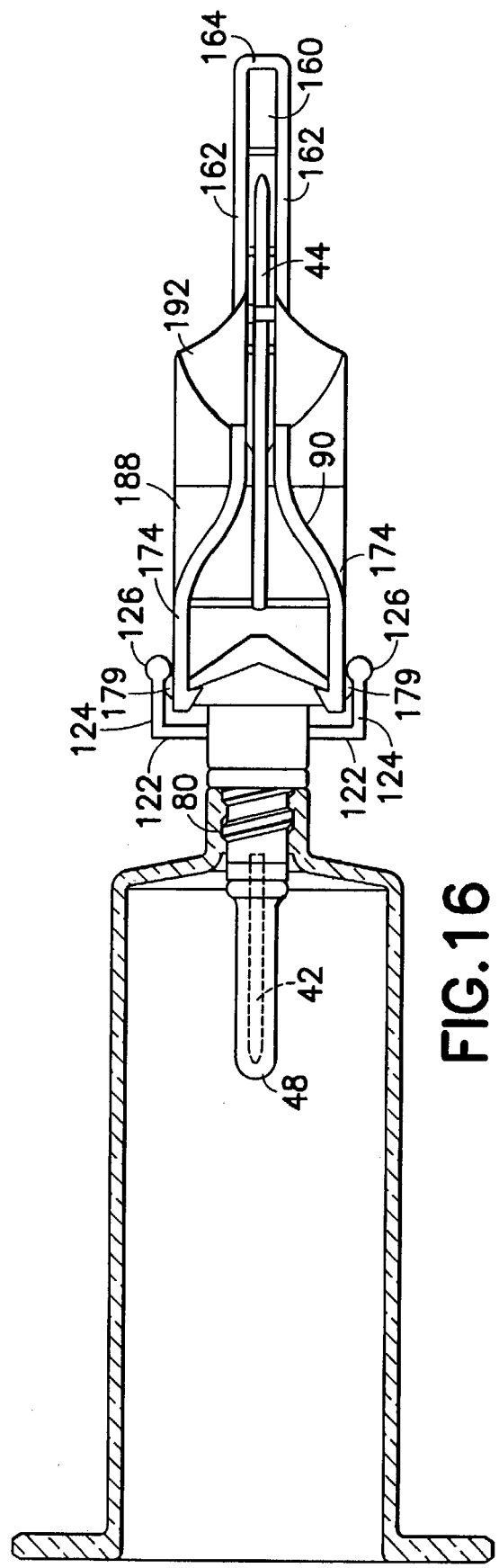
FIG. 16 is a bottom view of the assembly in use with a conventional needle holder with the shield in the shielded position as shown in FIG. 13.

In embodiments including a needle locking mechanism such as arm 167, the needle snaps past arm 167 and is trapped when needle 40 is contained within shield 140 as shield 140 is pivoted into the closed or shielded position, as shown in FIGS. 15 and 16. Alternatively, a gel material may be located in the shield near arm 167 so that when needle 40 snaps past arm 167, it will come to rest within the gel material. The gel material will contain any residual fluid that may be on needle 40.

FIGS. 17-40 are further embodiments of the invention that include many components which are substantially identical to the components of FIGS. 1-16. Accordingly, similar components performing similar functions will be numbered identically to those components of FIGS. 1-16, except that a suffix "a" will be used to identify those similar components in the embodiment of FIGS. 17-20, a suffix "b" will be used to identify those similar components in the embodiment of FIGS. 21-23, a suffix "c" will be used to identify those similar components in the embodiment of FIGS. 24-26, a suffix "d" will be used to identify those similar components in the embodiment of FIGS. 27-31, a suffix "e" will be used to identify those similar components in the embodiment of FIGS. 32-34, a suffix "f" will be used to identify those similar components in the embodiment of FIGS. 35-37, a suffix "g" will be used to identify those similar components in the embodiment of FIG. 38, a suffix "h" will be used to identify those similar components in the embodiment of FIG. 39, and a suffix "i" will be used to identify those similar components in the embodiment in FIG. 40.

FIGS. 17-37 depict further embodiments of needle shield assemblies and components thereof for attachment to and use with a needle assembly, such as a conventional double-ended phlebotomy needle as is known for use in blood collection procedures, a hypodermic needle for use with syringes, and the like. It is noted that the features of FIGS. 17-37 with respect to interlocking engagement between the collar and the shield are likewise practicable for use in connection with the needle assemblies depicted in connection with FIGS. 1-16.

Figure 17:
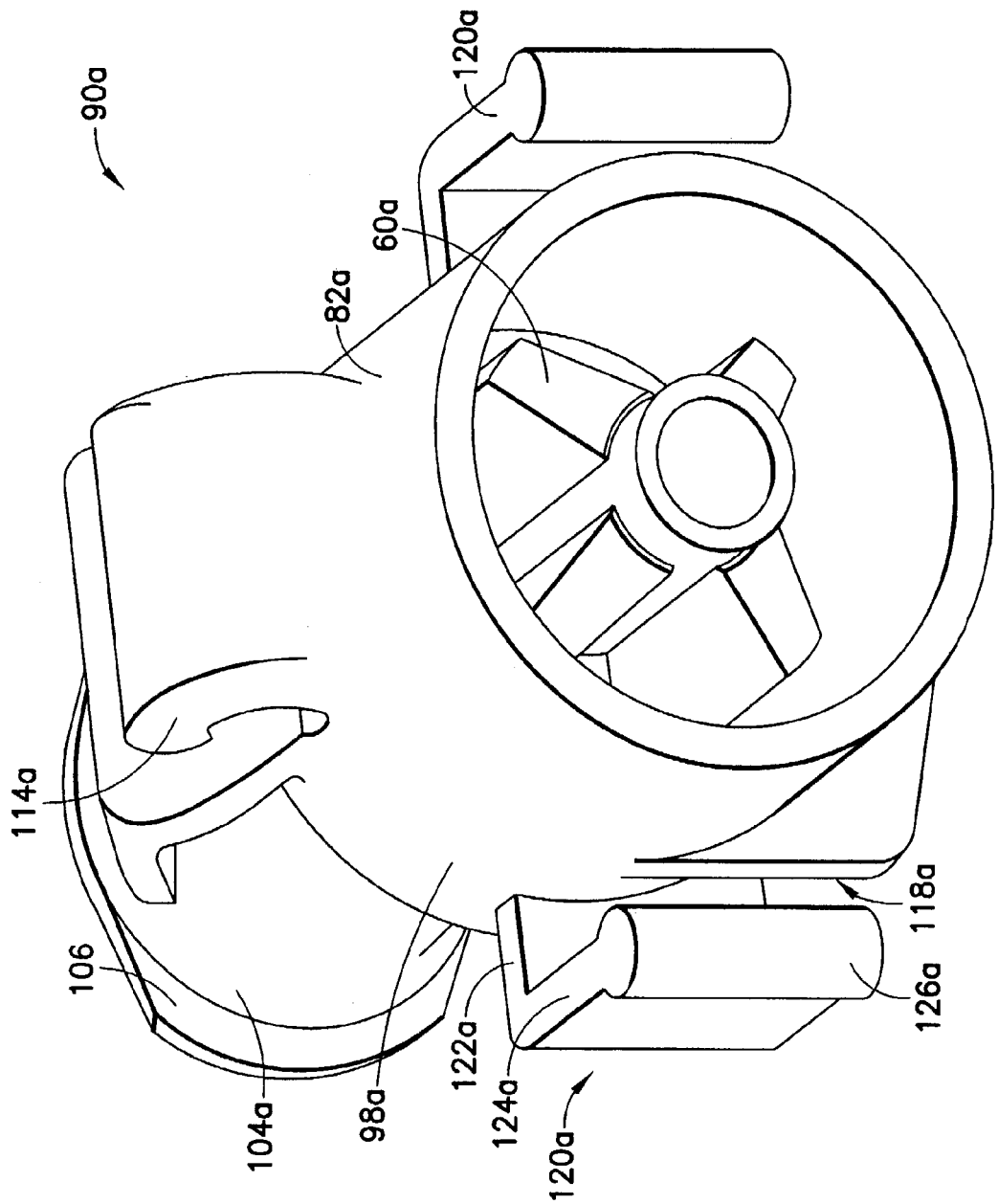
FIGS. 17 and 18 are top and bottom perspective views of an alternate collar in an alternate embodiment of the present invention.
Figure 18:
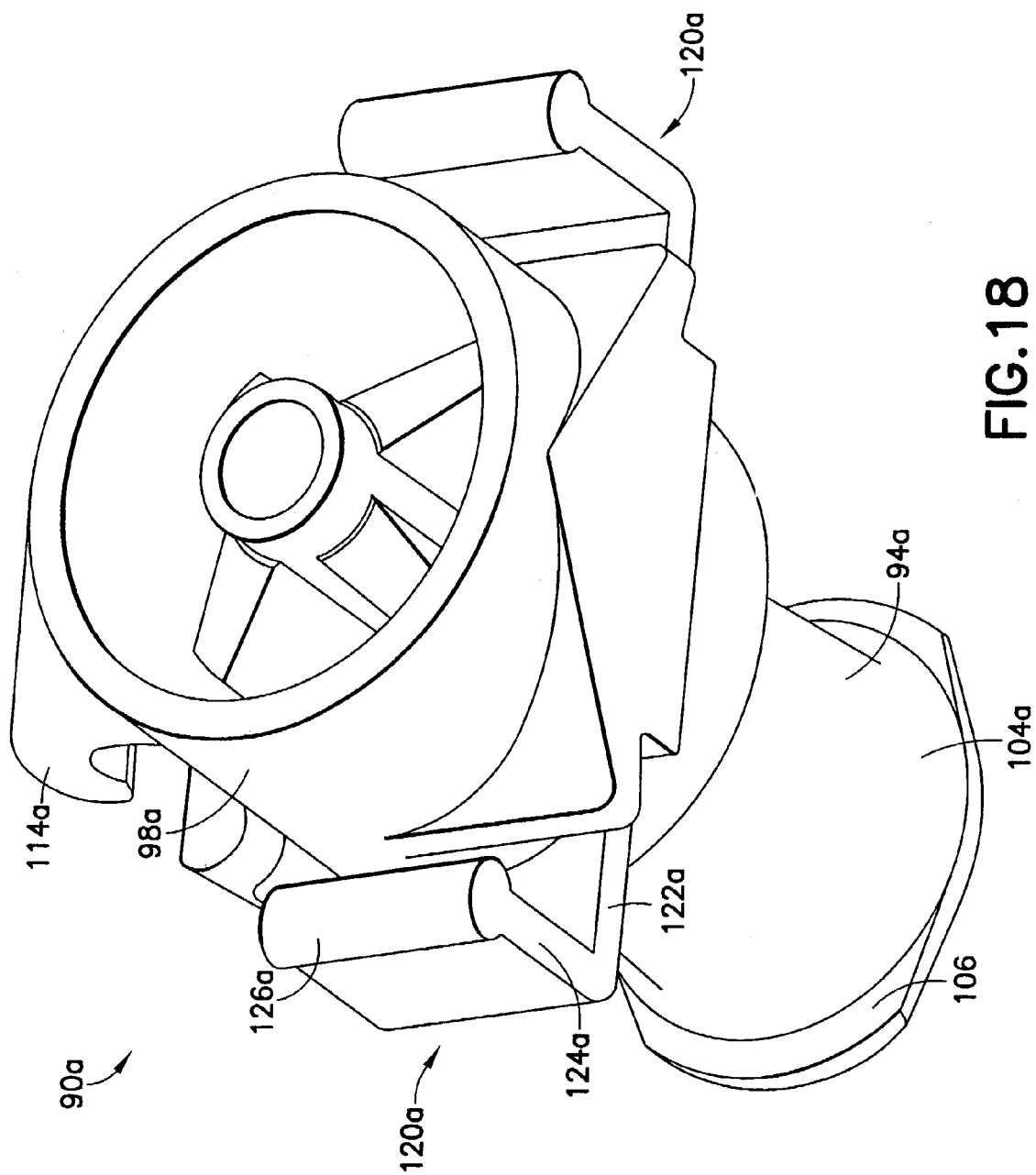
Figure 19:
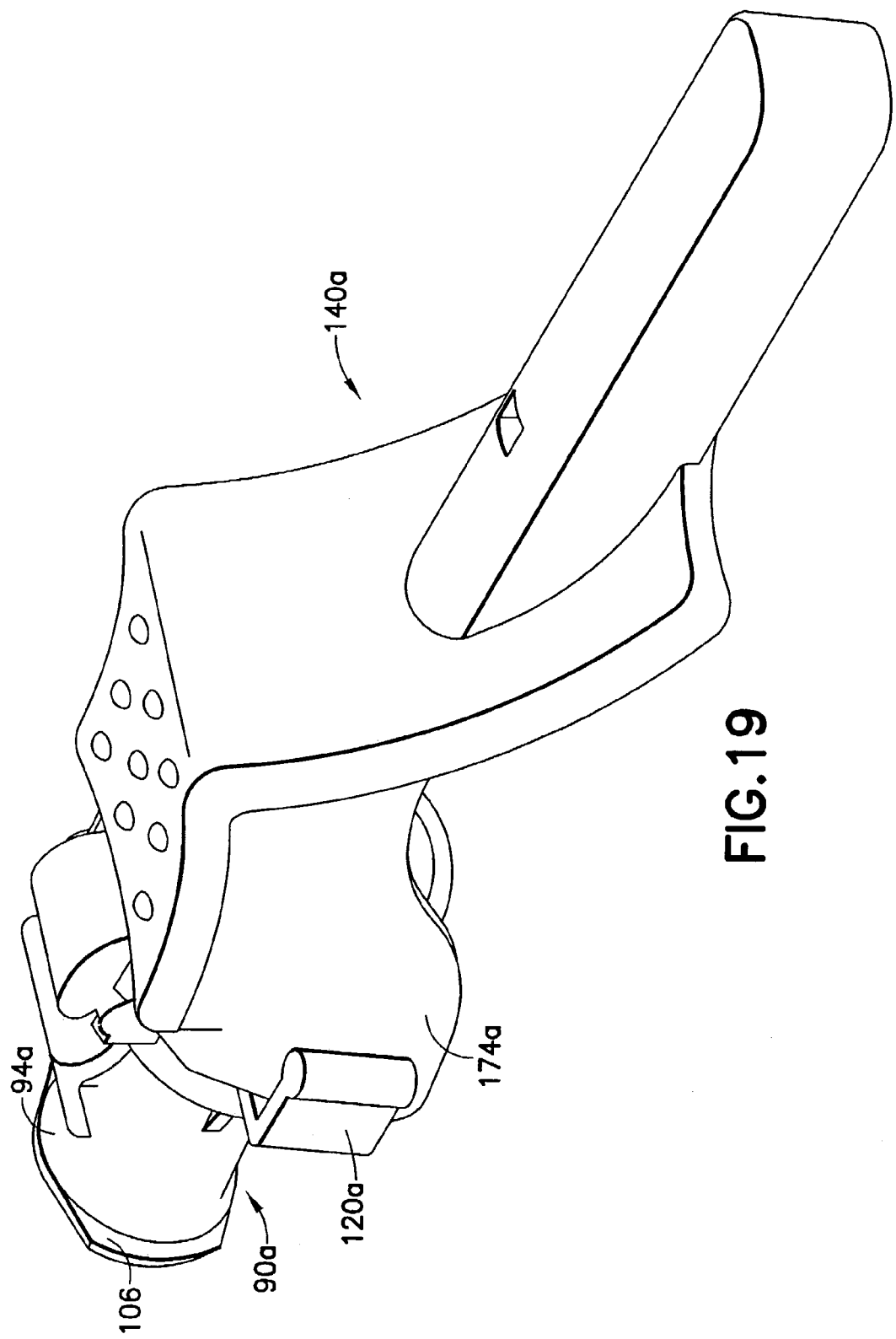
FIG. 19 is a front perspective view of a safety needle assembly in an alternate embodiment including the alternate collar as shown in FIGS. 17 and 18.
Figure 20:
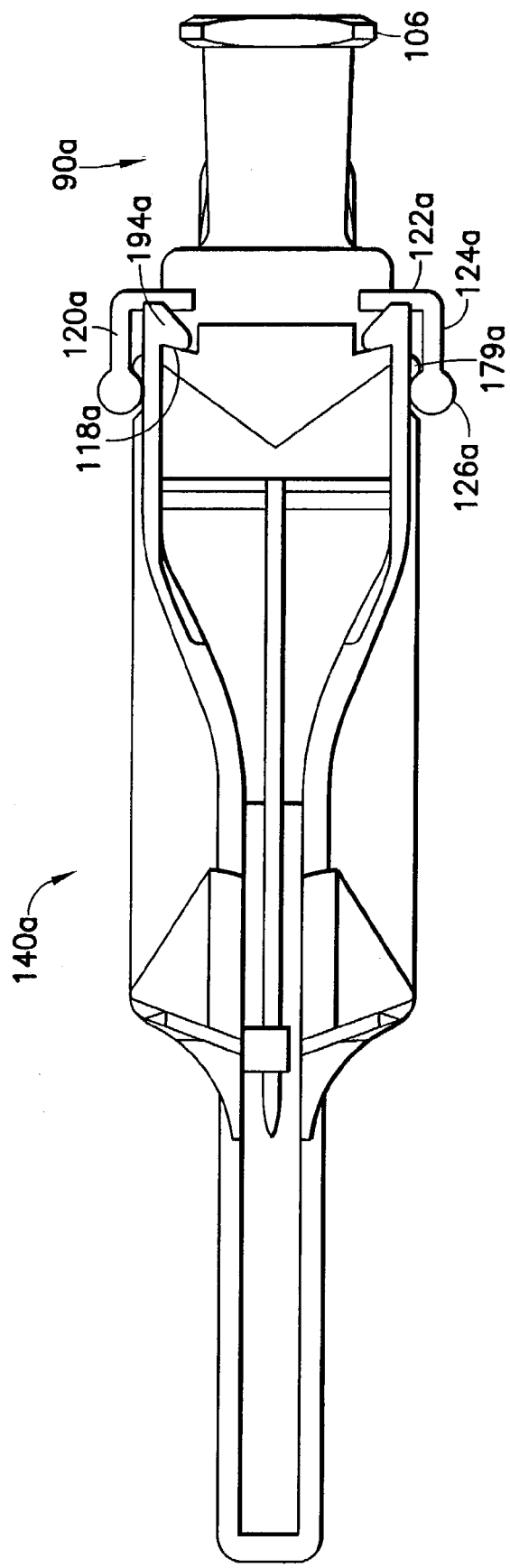
FIG. 20 is a bottom view of the alternate assembly of FIG. 19.

FIGS. 17-20 depict a shield assembly in an alternate embodiment of the present invention in which collar 90a is adapted for attachment to a conventional needle assembly. Collar 90a is shown in FIGS. 17-18 including hub 60a extending therein, but without any needle positioned within hub 60a, although such a needle would be provided in use thereof.

Collar 90a includes forward annular skirt 92a and rearward annular skirt 94a, as set forth above in connection with the embodiments described with reference to FIGS. 1-16. Rearward annular skirt 94a of collar 90a is provided for engagement with and attachment to a medical device, and may therefore comprise a luer fitting such as a female luer fitting, or the like. Rearward annular skirt 94a desirably includes a rearward flange 106, for assisting in attachment and removal of the shield assembly from an appropriate medical device.

Figure 21:
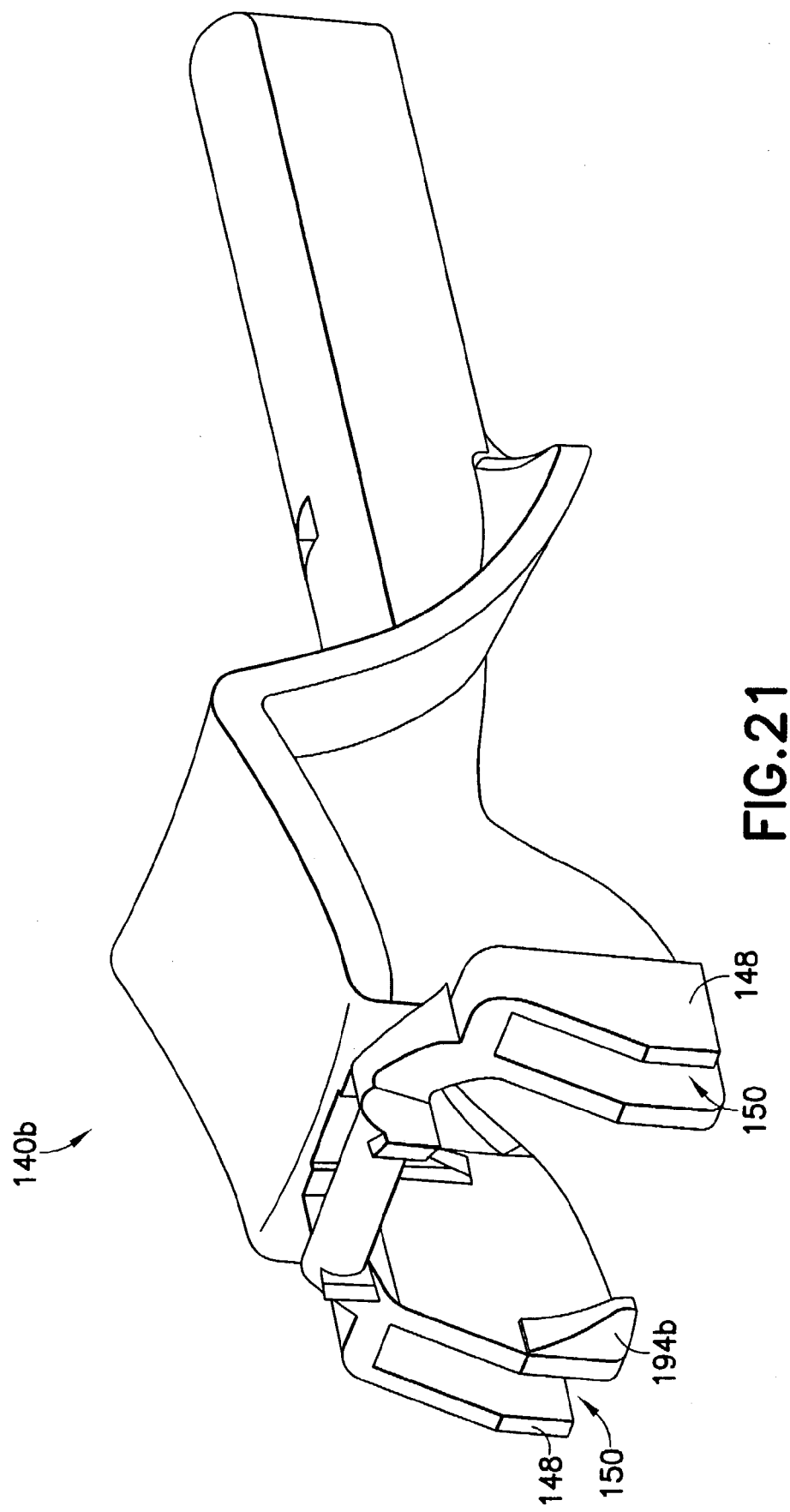
FIG. 21 is a rear perspective view of an alternate shield in a further embodiment of the present invention.
Figure 22:
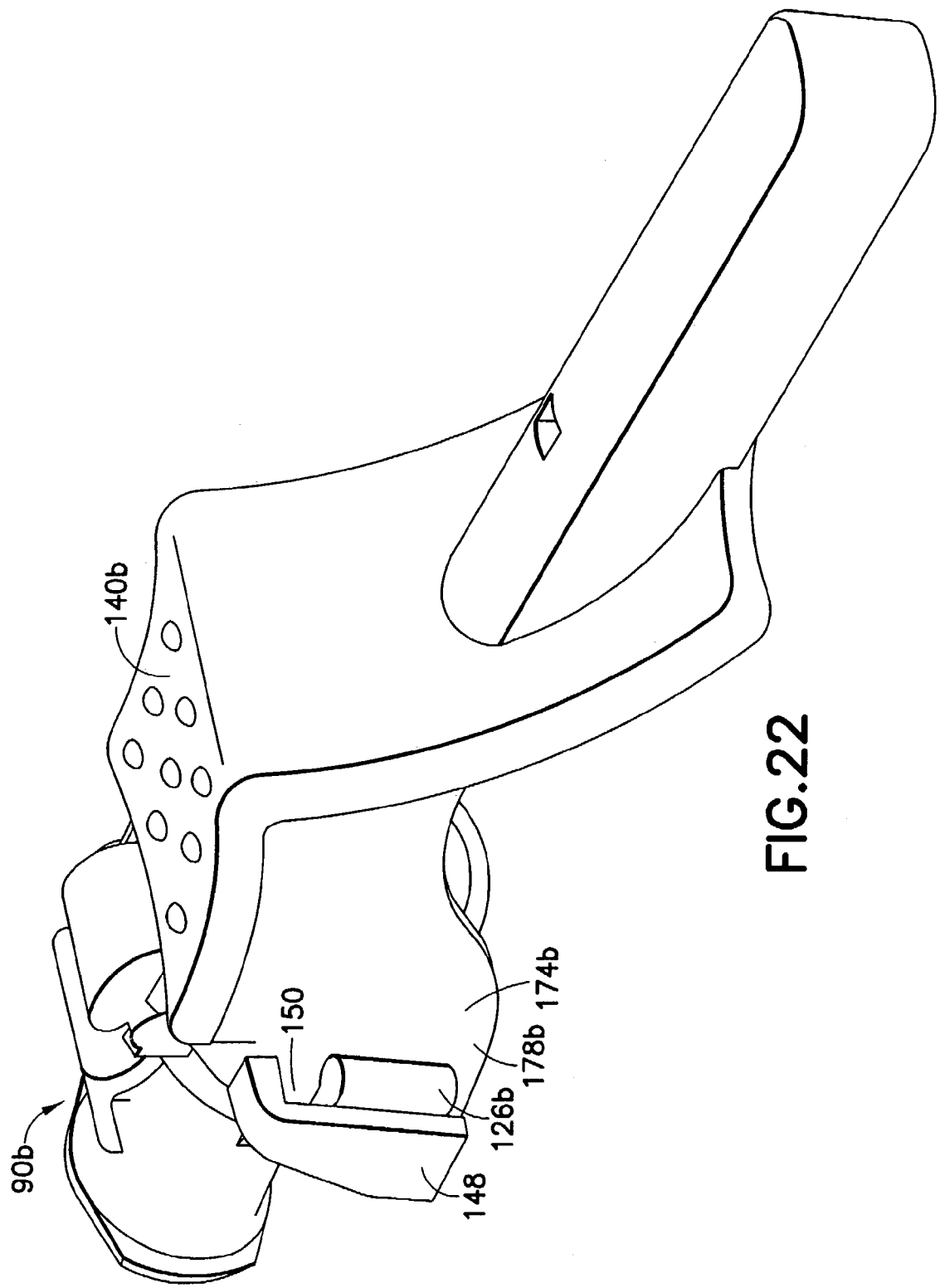
FIG. 22 is a front perspective view of a safety needle assembly in an alternate embodiment including the alternate shield as shown in FIG. 21.
Figure 23:
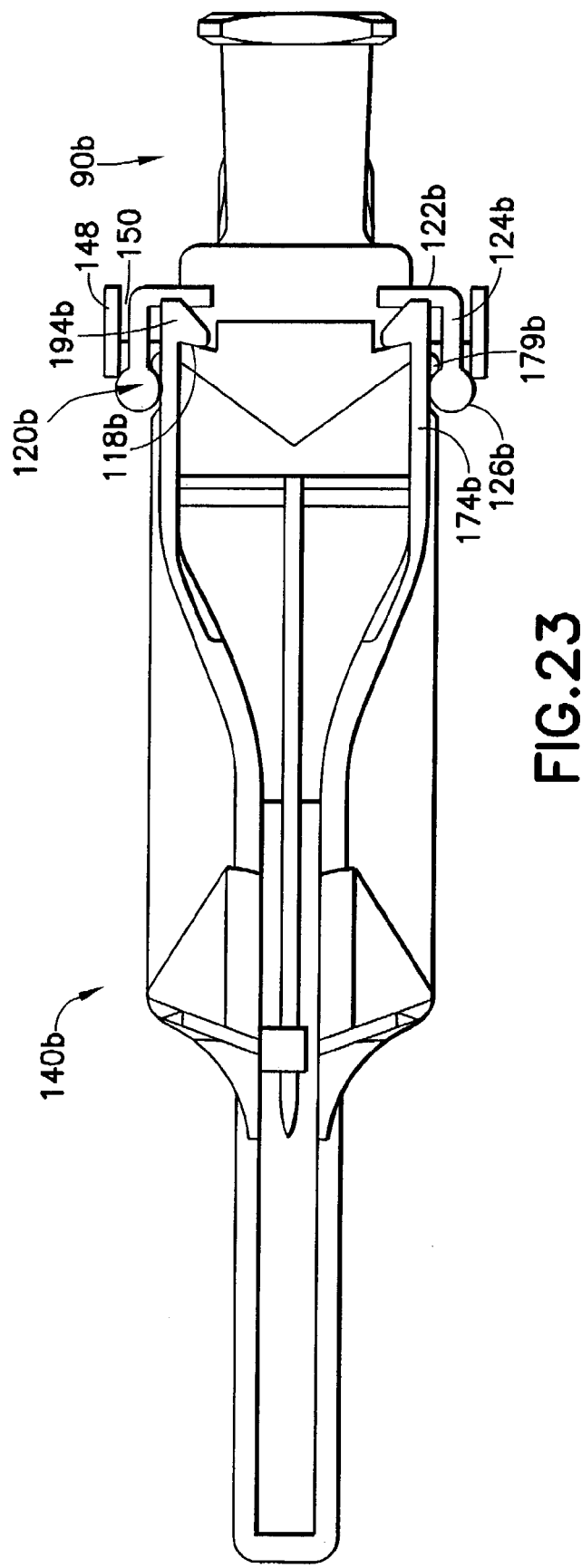
FIG. 23 is a bottom view of the alternate assembly of FIG. 21.

In FIGS. 21-23, shield 140b further includes outer shield flange 148 extending downwardly from an outer surface 178b of at least one, and preferably both of parallel sidewalls 174b of shield 140b, establishing interior openings 150 between outer shield flanges 148 and outer surface 178b of parallel sidewalls 174b. Outer shield flanges 148 may be a flexible material. During pivotal rotation of shield 140b to the shielded position, outer shield flanges 148 rotate over collar flanges 120b, with collar flanges 120b fitting within interior openings 150 between outer shield flanges 148 and parallel sidewalls 174b. Rounded forward edge 126b assures that collar flanges 120b easily travel through interior openings 150 without interruption. As seen in FIG. 23, collar flanges 120b protectively surround the locking engagement area between barb dents 194b and locking dents 118b and therefore prevent disengagement therebetween, with outer shield flanges 148 further providing protection for the locking engagement area.

Figure 24:
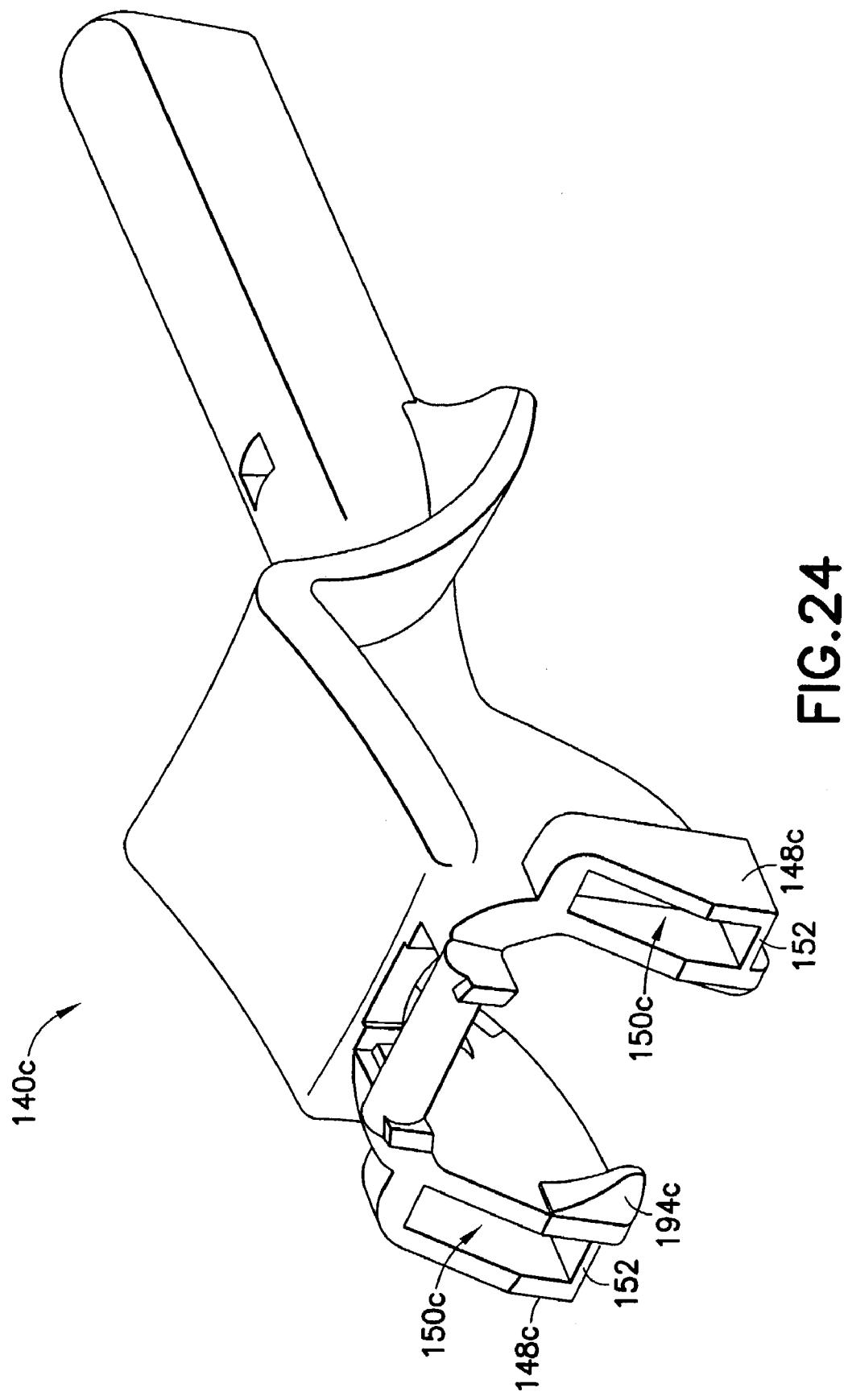
FIG. 24 is a rear perspective view of an alternate shield in yet a further embodiment of the present invention.
Figure 25:
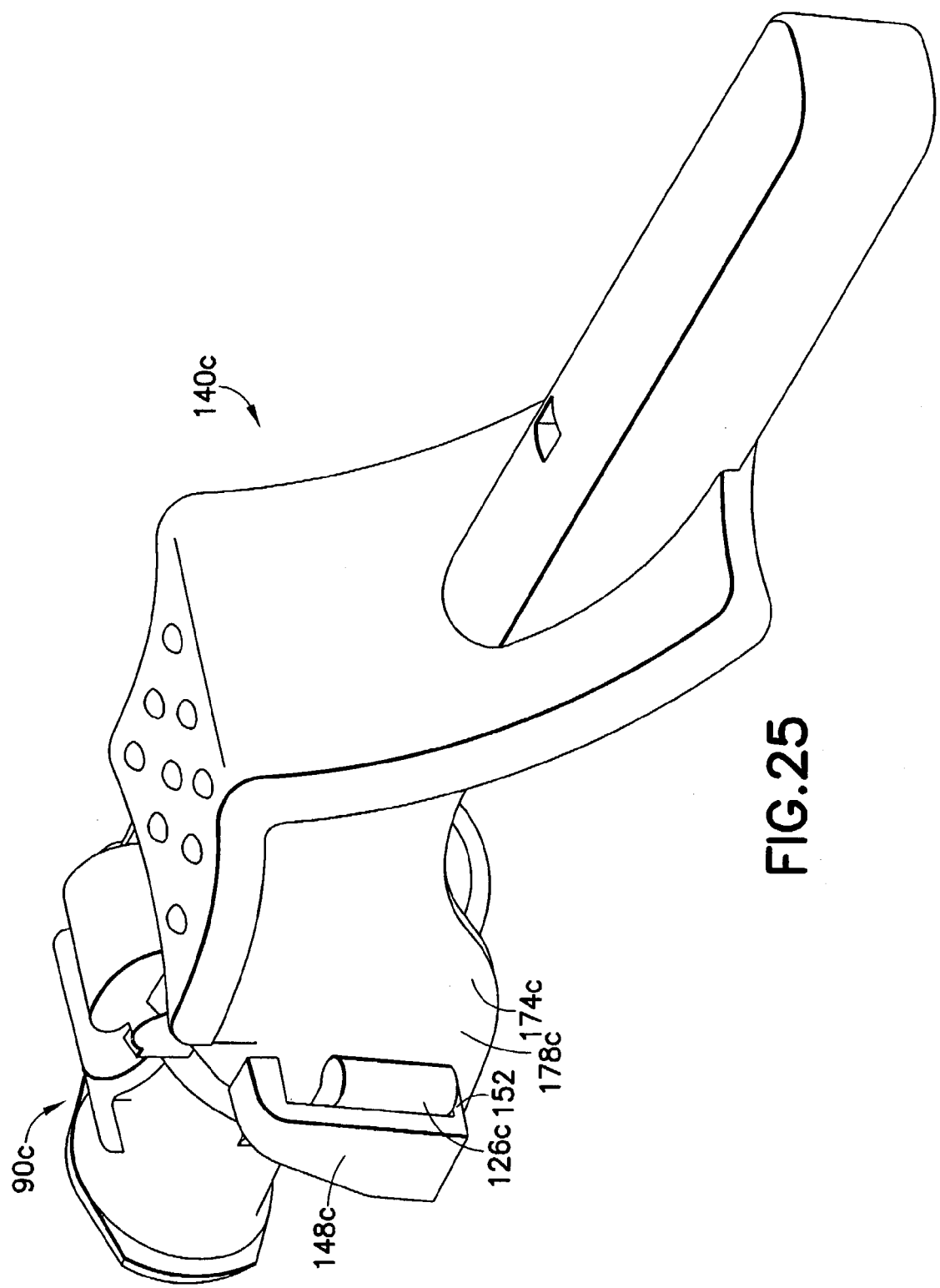
FIG. 25 is a front perspective view of a safety needle assembly in an alternate embodiment including the alternate shield as shown in FIG. 24.
Figure 26:
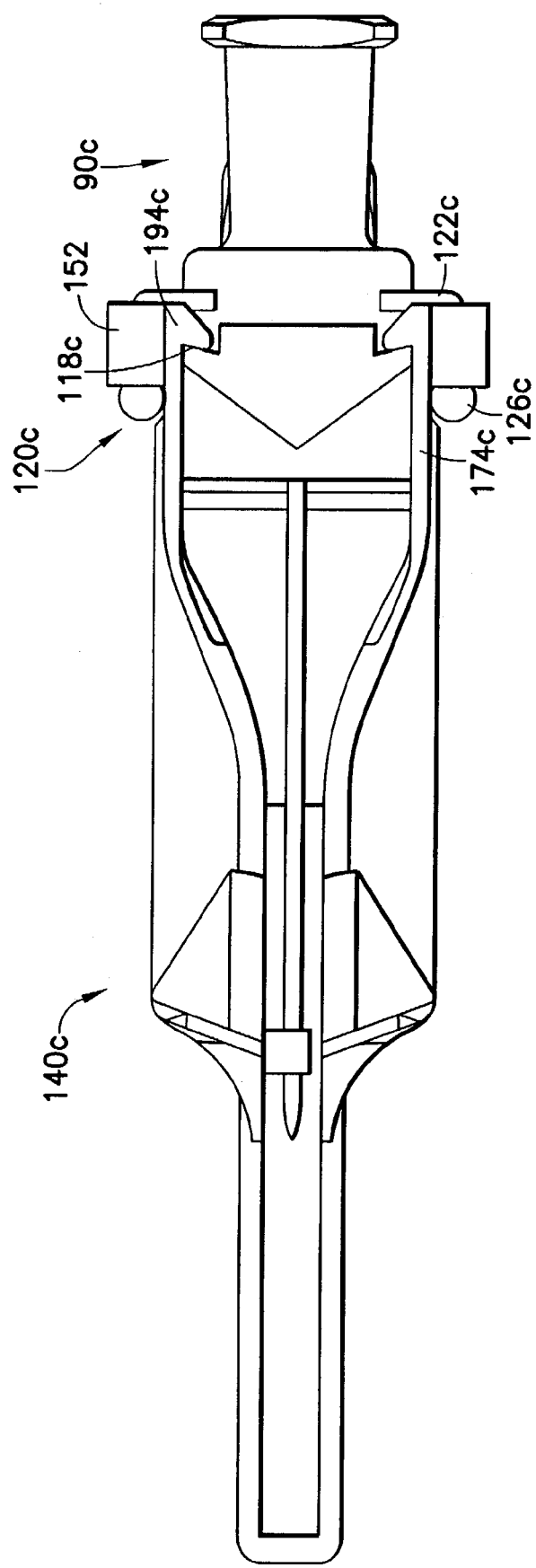
FIG. 26 is a bottom view of the alternate assembly of FIG. 25.
Figure 27:
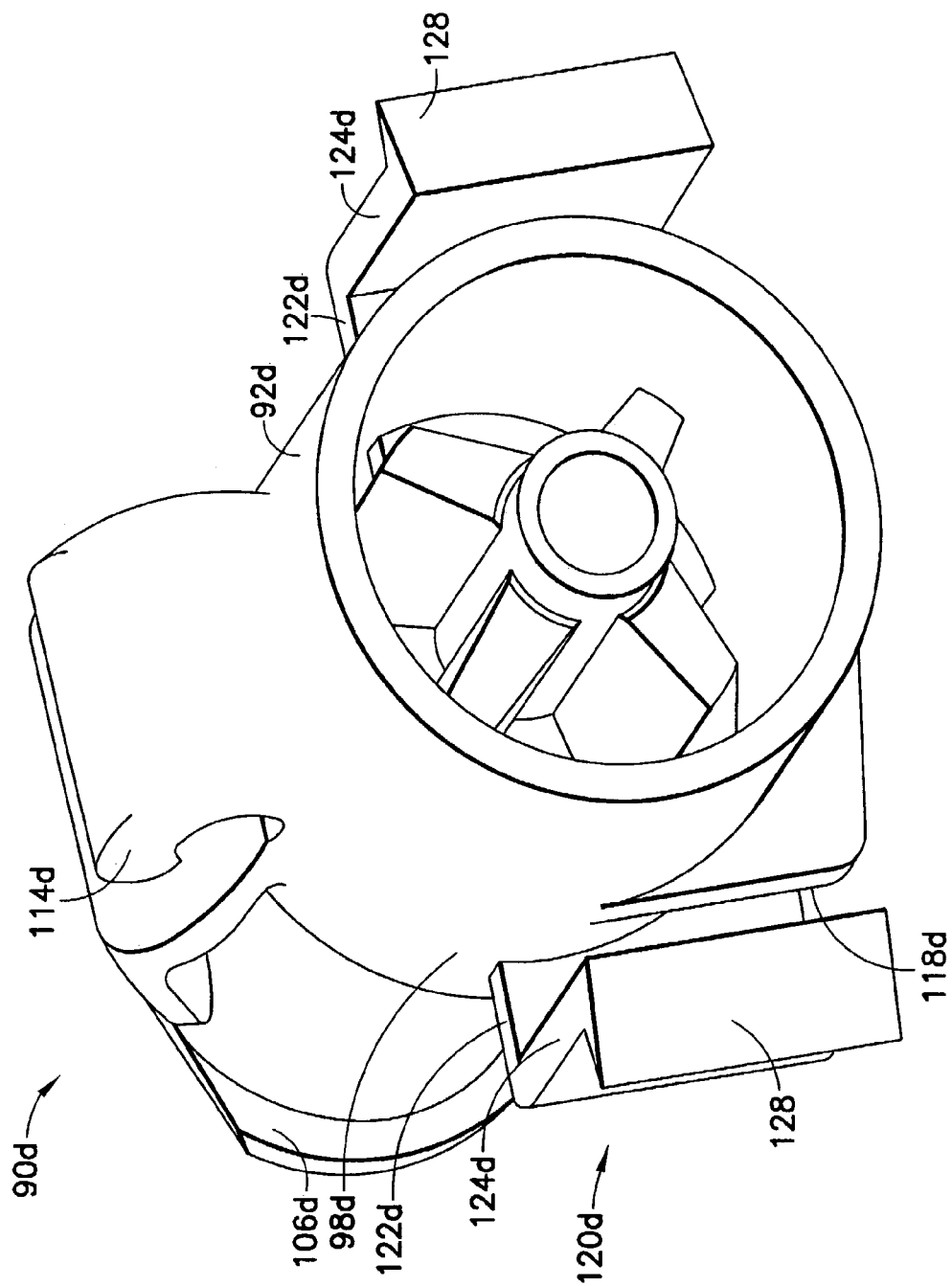
FIGS. 27 and 28 are top and bottom perspective views of a further alternate collar in an alternate embodiment of the present invention.
Figure 28:
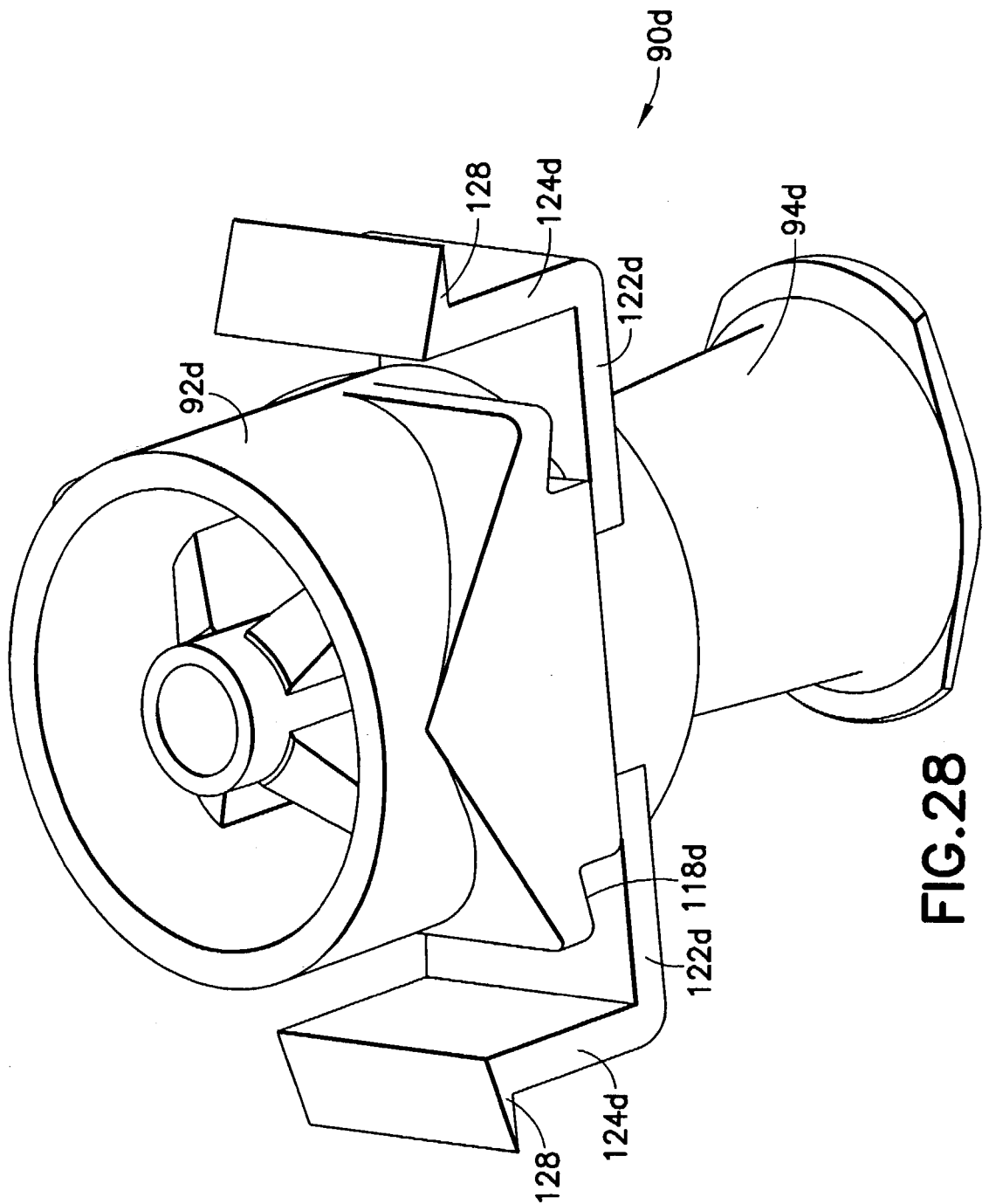

FIGS. 24-26 depict a shield 140c which includes outer shield flanges 148c in a similar manner as in FIGS. 21-23, and further includes connecting members 152 extending between the bottom edge of outer shield flanges 148c and parallel sidewalls 174c. By providing connecting members 152 in this manner, interior openings 150c formed between outer shield flanges 148c and outer surface 178c of parallel sidewalls 174c are completely enclosed, providing a complete enclosure for collar flanges 120c to fit within, and providing additional structural rigidity to the rearward end of shield 140c surrounding the locking engagement area.

Figure 29:
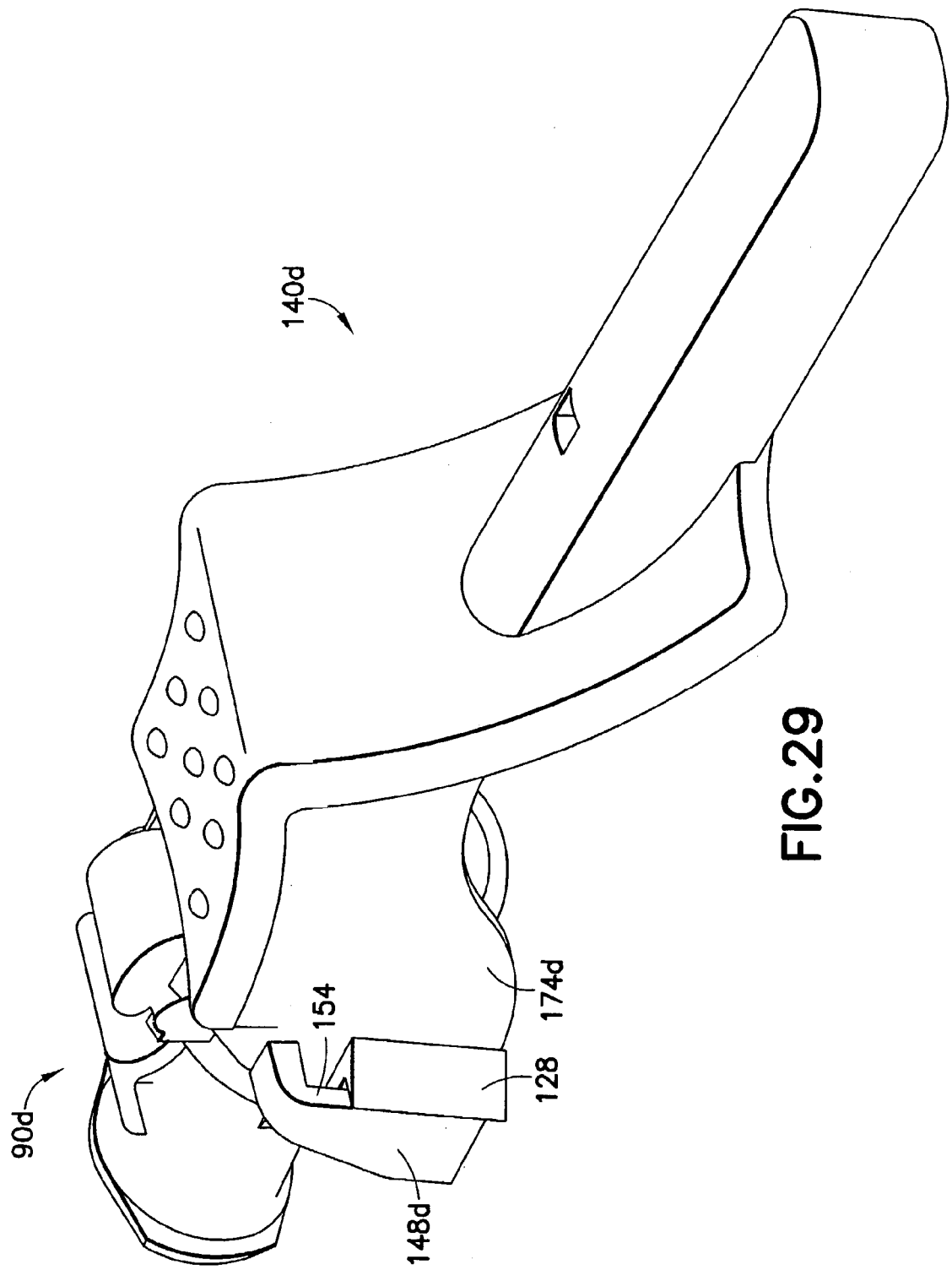
FIG. 29 is a front perspective view of a safety needle assembly in an alternate embodiment including the alternate collar as shown in FIGS. 27 and 28 in combination with the alternate shield as shown in FIG. 21.
Figure 30:
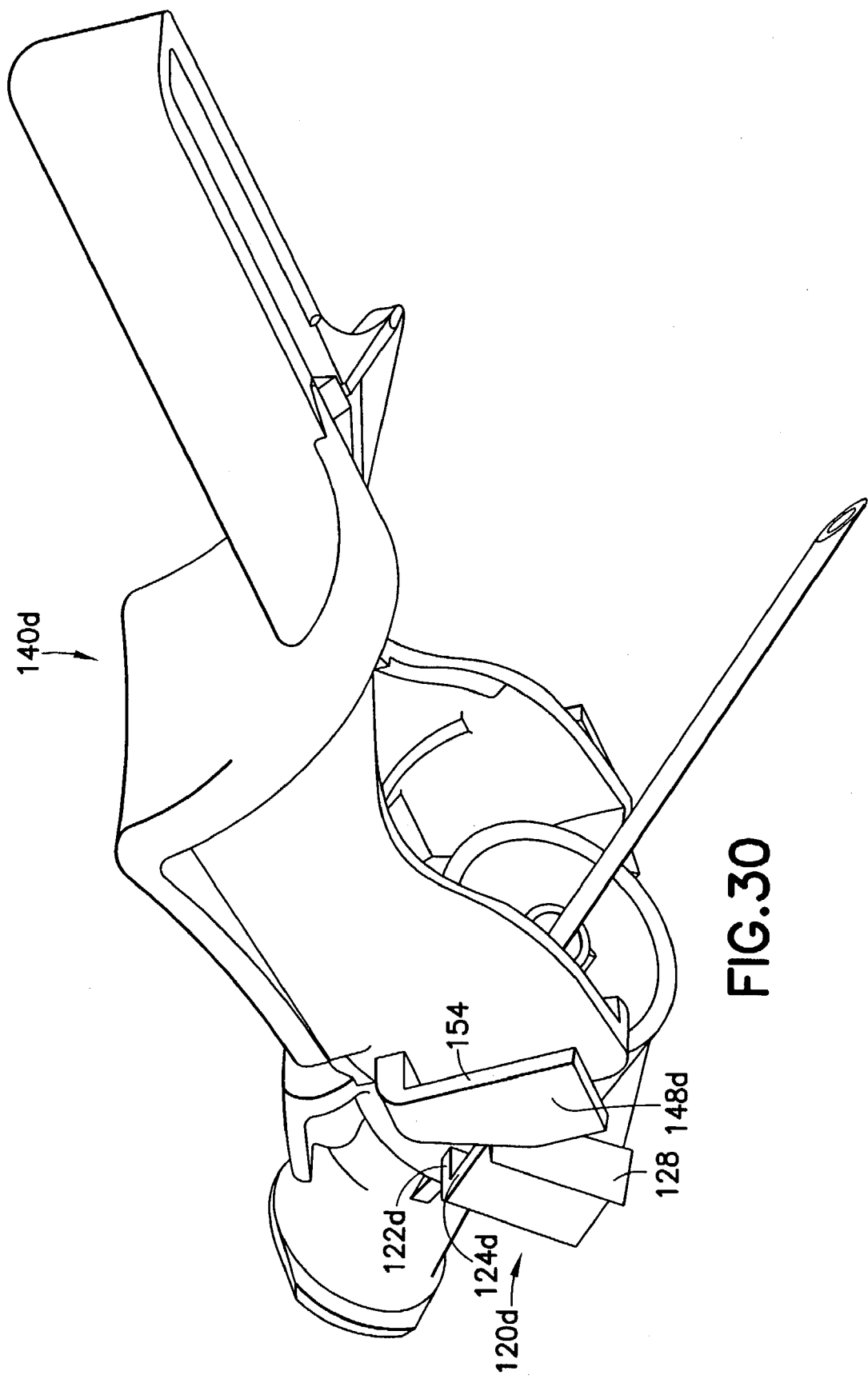
FIG. 30 is a front bottom perspective view of the assembly of FIG. 29 shown with the shield in a retracted position.
Figure 31:
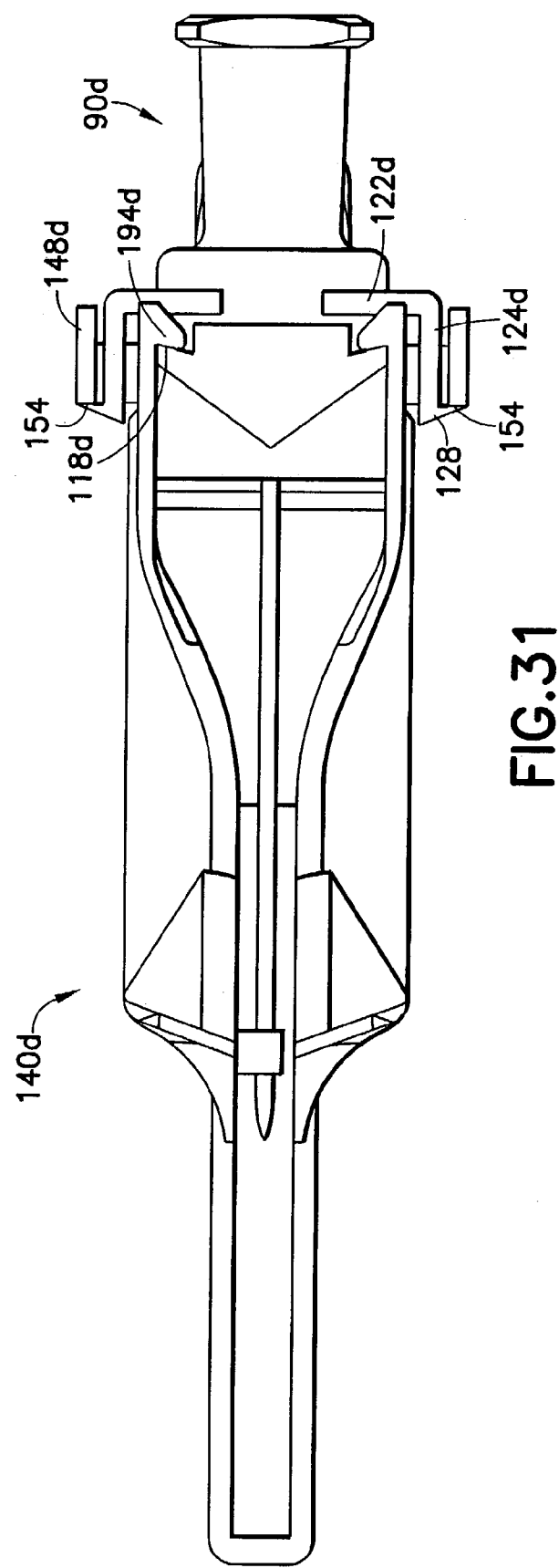
FIG. 31 is a bottom view of the alternate assembly of FIG. 29.

FIGS. 27-31 depict a shield assembly in a further embodiment of the present invention, in which collar 90d includes collar flanges 120d having outer flange latches 128 externally disposed at the forward end of forward extending portion 124d. Outer flange latches 128 are provided for locking engagement with an outer flange edge 154 of outer shield flange 148d, as shown in FIGS. 29 and 31. The interfitting engagement of outer flange latches 128 and the outer flange edge of outer shield flange 148d provides for an irreversible locking engagement between shield 140 and the collar 90, and may provide a tactile feel to the user to indicate that the shield has been pivotally rotated to the fully shielded position.

Such locking engagement between outer flange latches 128 and outer flange edges 154 may provide the sole manner of locking engagement between shield 140d and collar 90d. Alternatively, as shown through FIG. 31, shield 140d and collar 90d are provided with two distinct sets of interengaging locking structures, including a first set of locking structures provided through barb dents 194d and locking dents 118d, which establishes a mechanism for shield 140d to latch onto collar 90d, and a second set of locking structures provided through outer flange latches 128 and outer flange edges 154, which establishes a mechanism for collar 90d to latch onto shield 140d. Accordingly, the assembly is provided with equal and opposite locking structure with collar 90d latching onto shield 140d and shield 140d latching onto collar 90d, thereby providing effective and secure irreversible locking interengagement therebetween.

Figure 32:
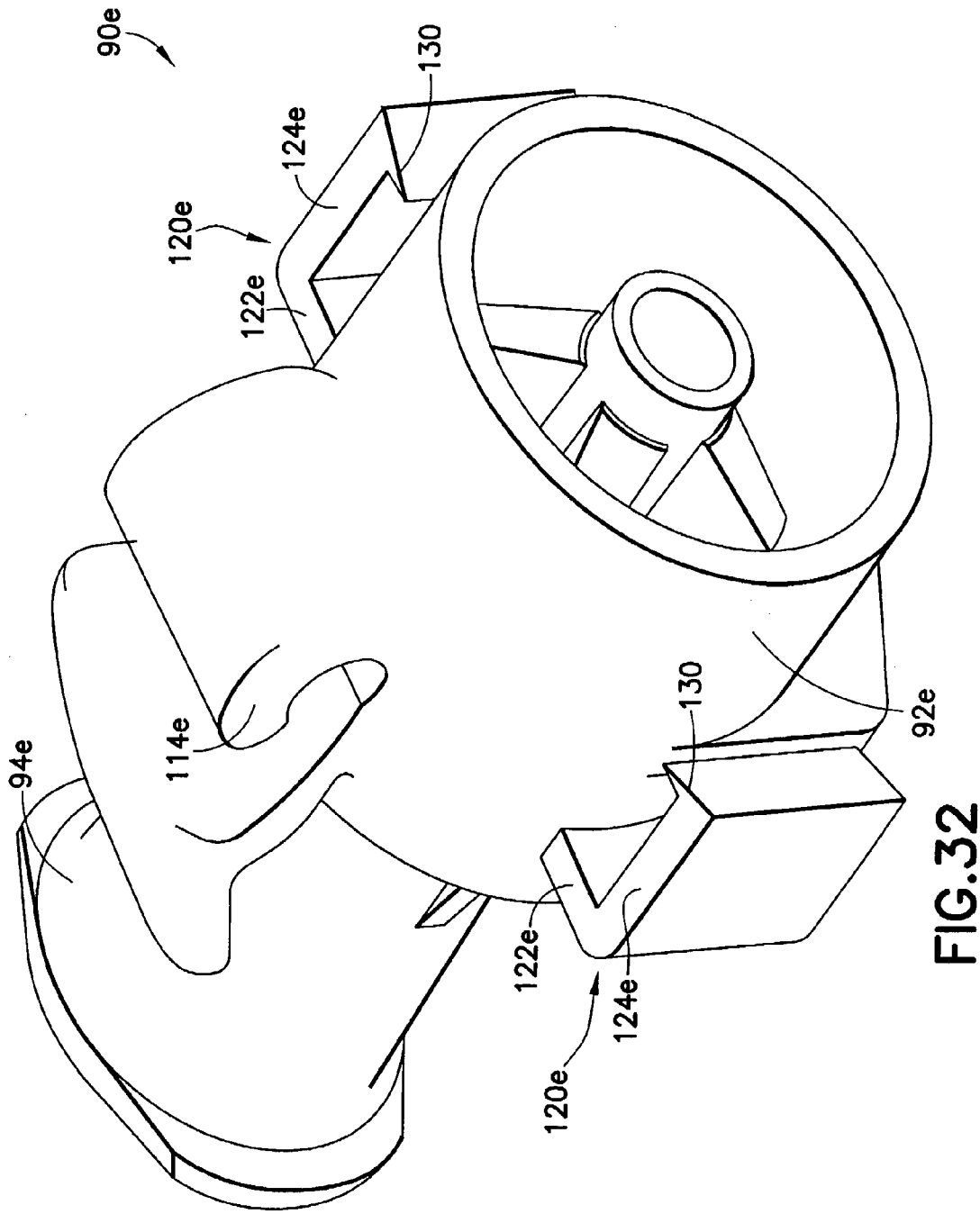
FIG. 32 is a top perspective view of yet a further alternate collar in an alternate embodiment of the present invention.
Figure 33:
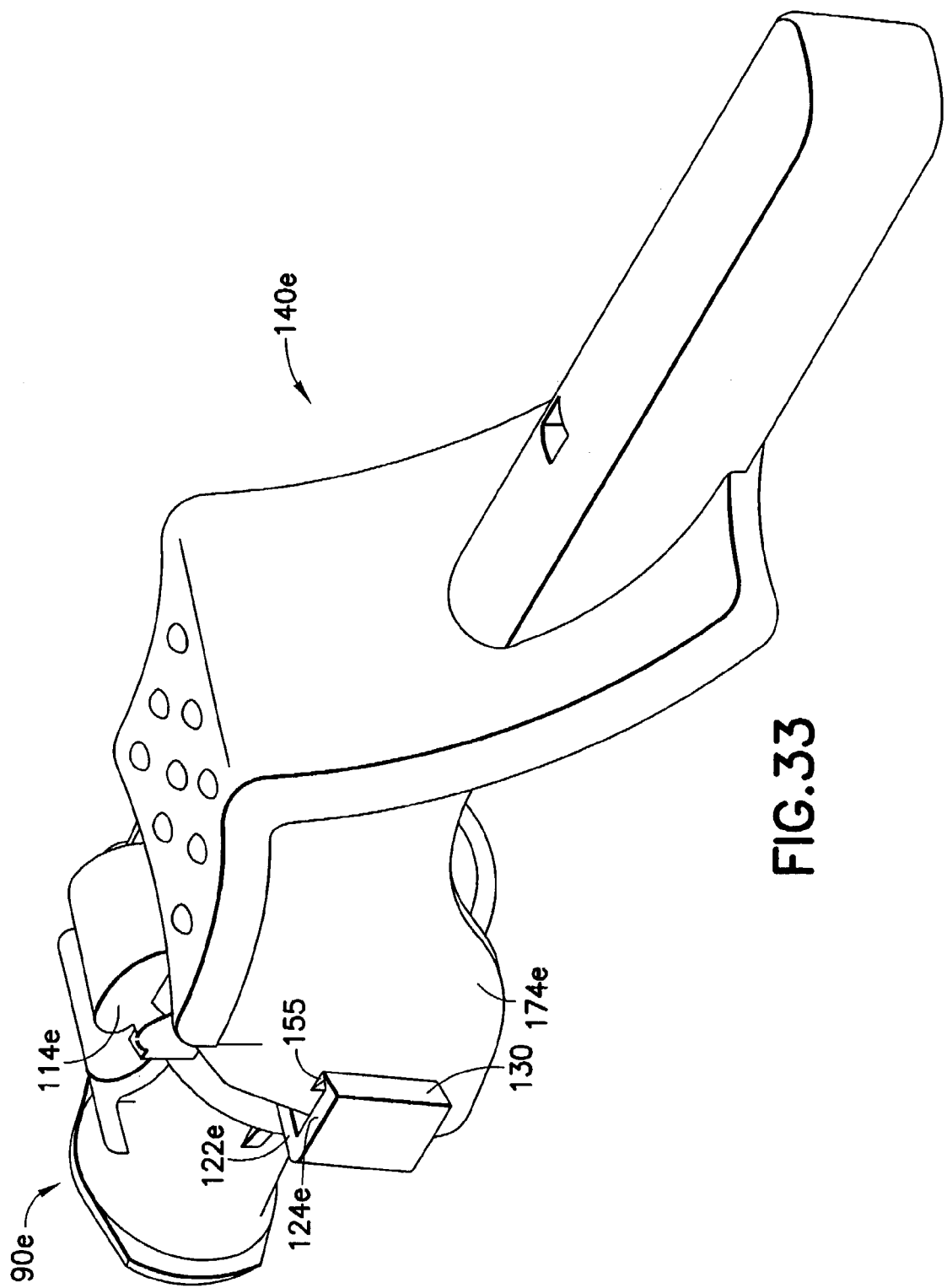
FIG. 33 is a front perspective view of a safety needle assembly in an alternate embodiment including the alternate collar as shown in FIG. 32 in combination with a shield.
Figure 34:
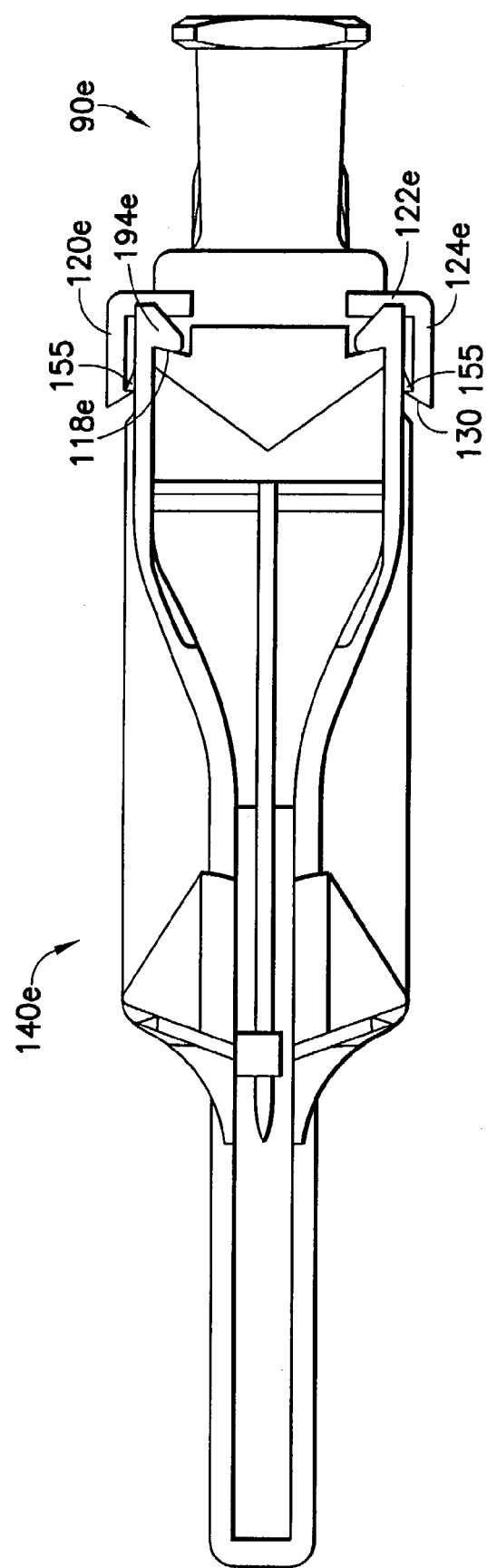
FIG. 34 is a bottom view of the alternate assembly of FIG. 33.

In the embodiment of FIGS. 32-34, collar 90e includes collar flanges 120e having inner flange latches 130 internally disposed at the forward end of forward extending portion 124e. Inner flange latches 130 are provided for locking engagement with shield lips 155, as shown in FIGS. 33 and 34. Such locking engagement between inner flange latches 130 and shield lips 155 provides for an irreversible locking engagement between shield 140 and collar 90, and may provide a tactile feel to the user to indicate that shield 90 has been pivotally rotated to the fully shielded position.

Figure 35:
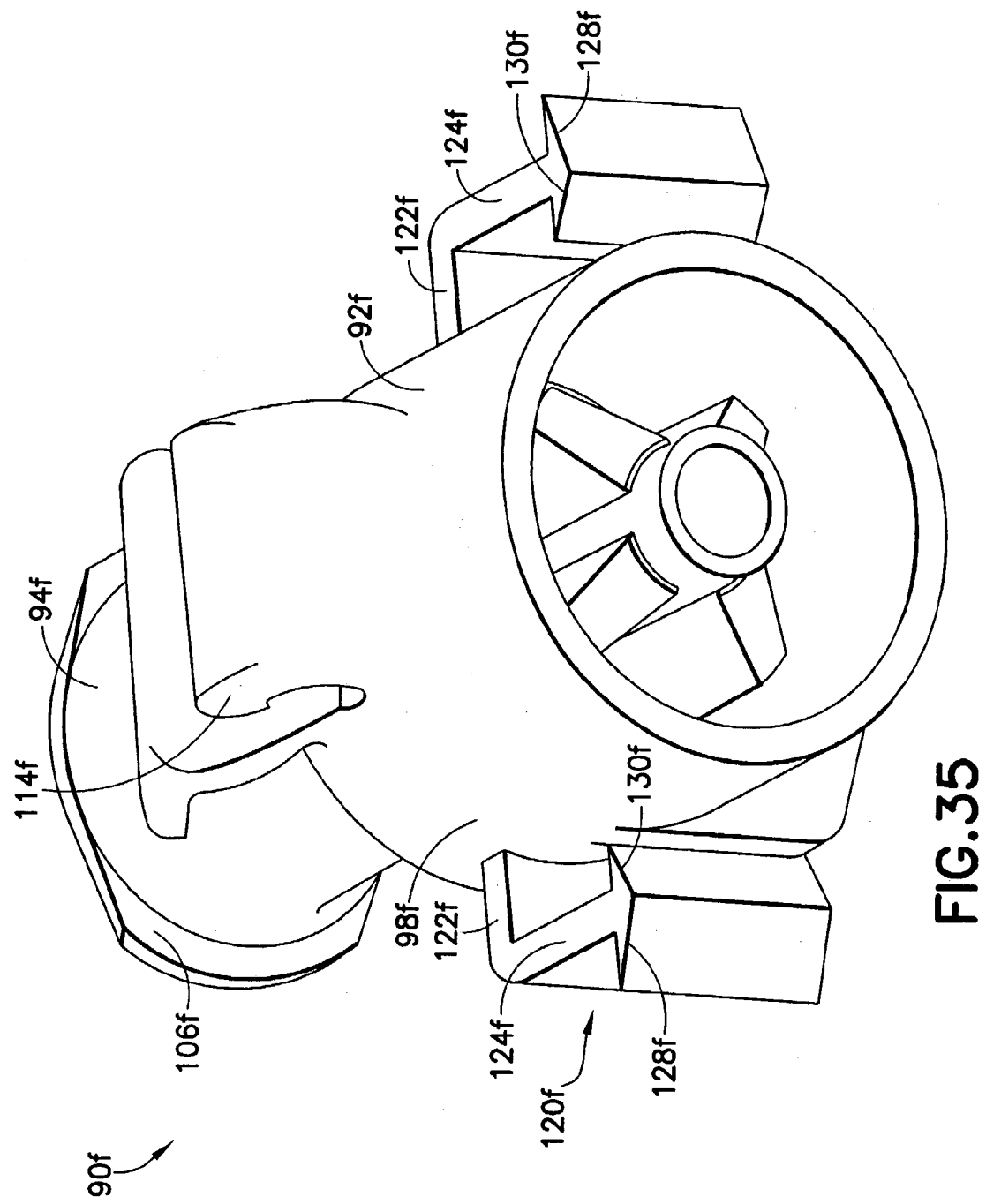
FIG. 35 is a top perspective view of yet a further alternate collar in an alternate embodiment of the present invention.
Figure 36:
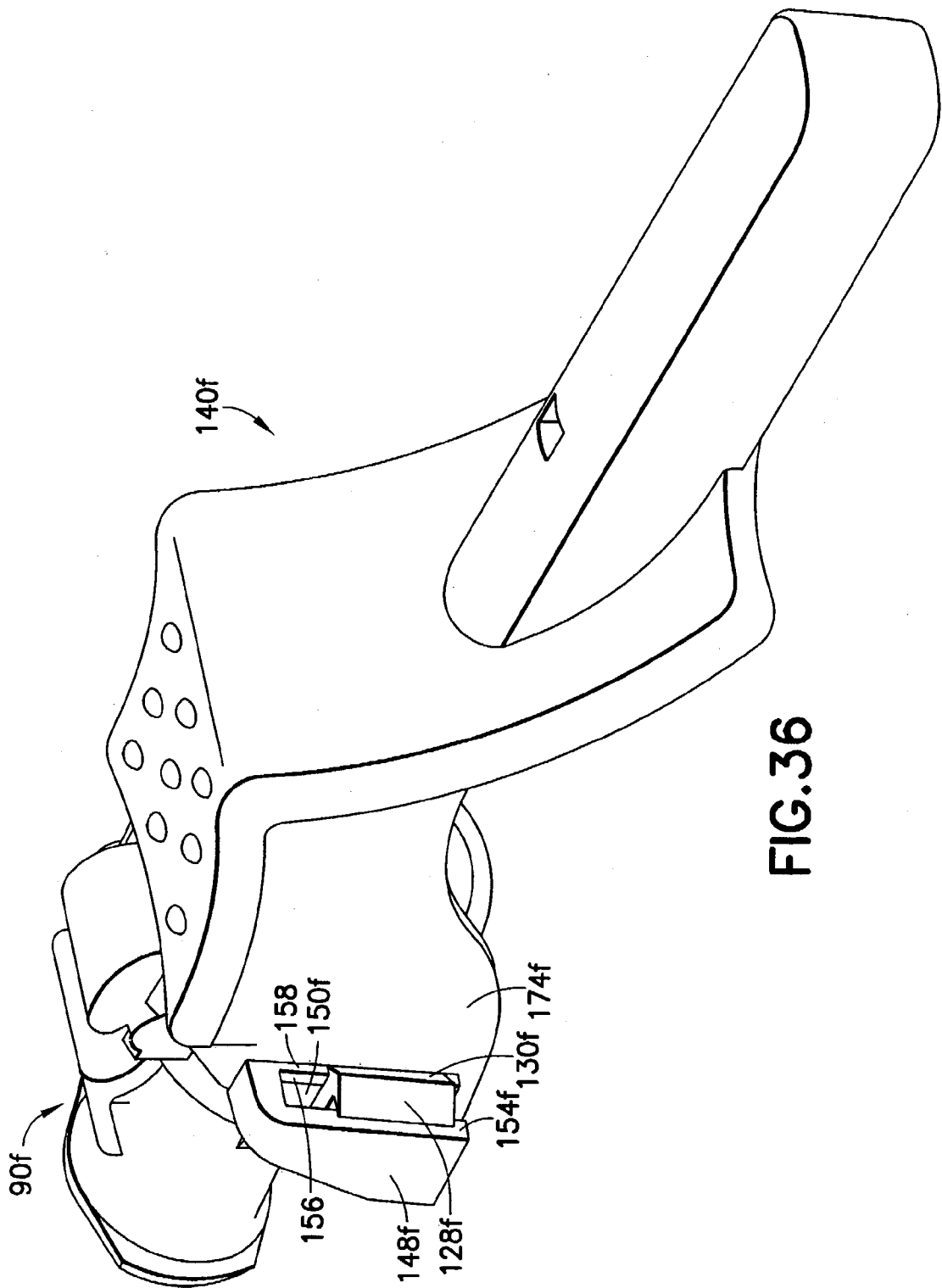
FIG. 36 is a front perspective view of a safety needle assembly in an alternate embodiment including the alternate collar as shown in FIG. 35 in combination with the alternate shield as shown in FIG. 21.
Figure 37:
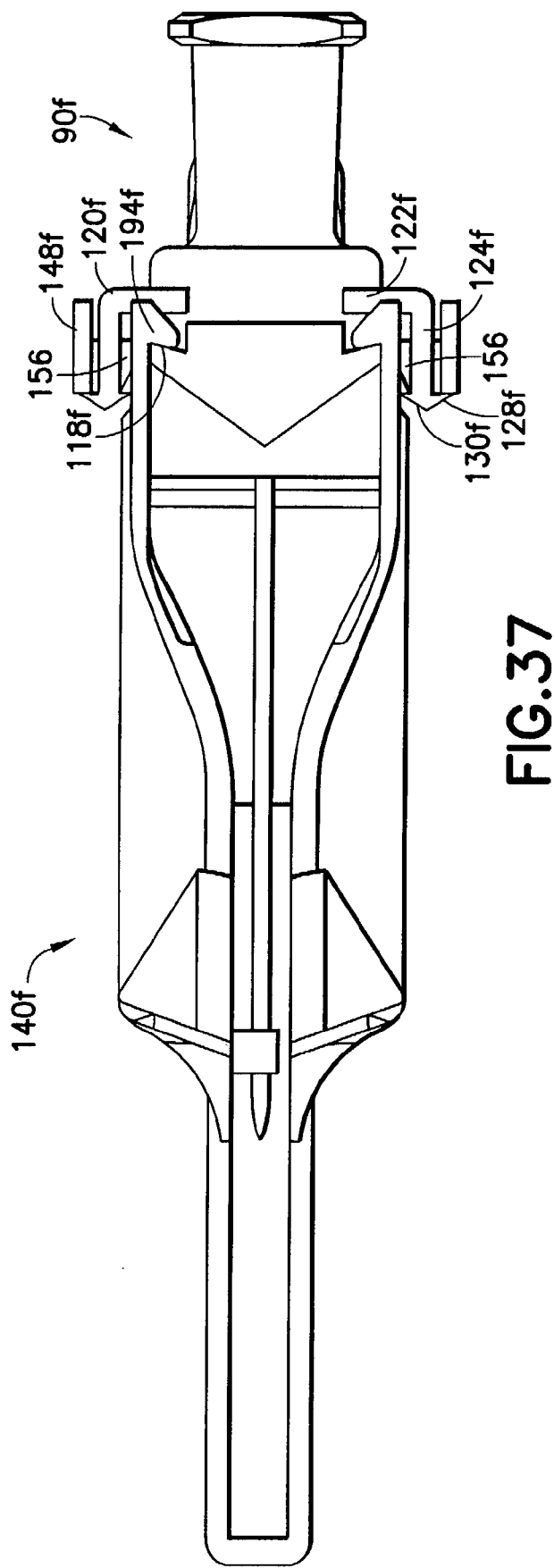
FIG. 37 is a bottom view of the alternate assembly of FIG. 36.

FIGS. 35-37 depict a further embodiment, in which collar 90f includes collar flanges 120f having both outer flange latches 128f and inner flange latches 130f. In addition, shield 140f depicted in FIGS. 36 and 37 includes a pair of outer shield flanges 148f extending from outer surface 178f of parallel sidewalls 174f, and may further include a pair of inner shield flanges 156 which are integral with outer surface 178f of parallel sidewalls 174f. These inner shield flanges 156 function in a similar manner as shield lips 155 described with respect to FIGS. 32-34, providing a surface for locking engagement with inner flange latches 130f. It is noted that either shield lips 155 or inner shield flanges 156 may be incorporated into embodiments including inner flange latches for locking engagement therewith. During pivotal rotation of shield 140f with respect to collar 90f, collar flanges 120f extend through openings 150f between outer shield flanges 148f and inner shield flanges 156. Outer shield flange 148f may slightly flex to allow collar flange 120f to pass through opening 150f, or outer flange latches 128f and inner flange latches 130f may slightly flex or deform to pass through and beyond opening 150f, to engage with outer flange edge 154f and inner flange edge 158. Such engagement provides for an irreversible locking engagement between shield 140d and collar 90d, and may provide a tactile feel to the user to indicate that shield 140d has been pivotally rotated to the fully shielded position.

Figure 38:
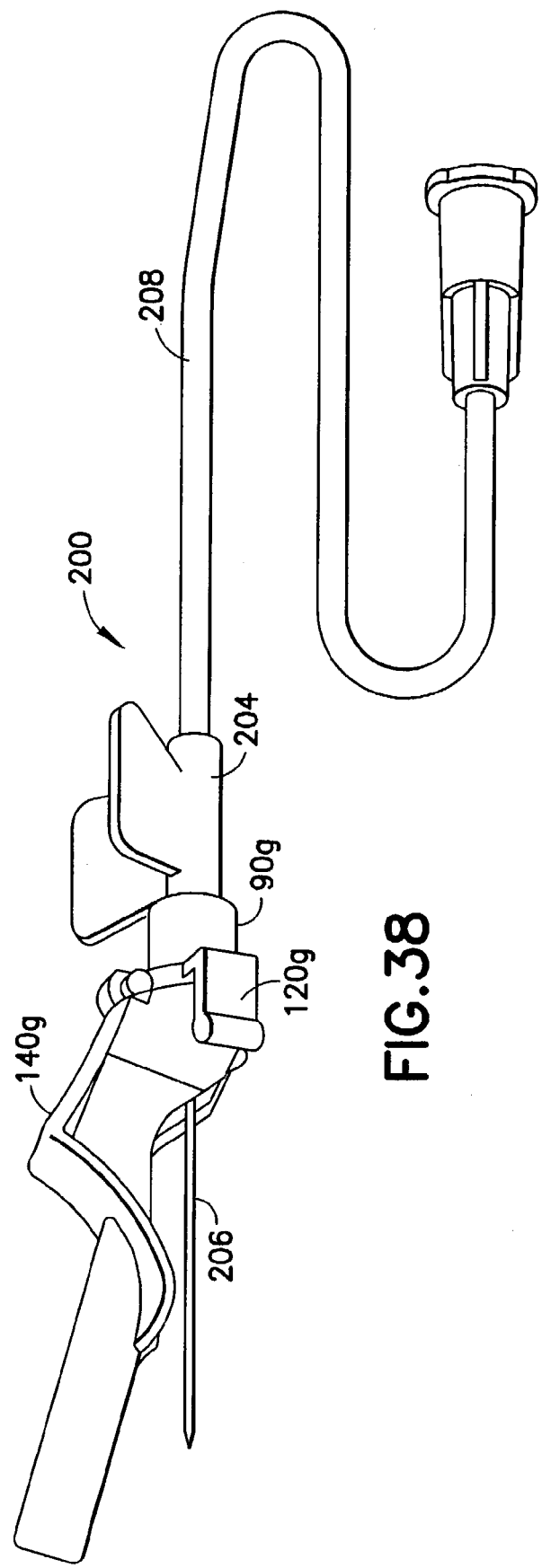
FIG. 38 is a perspective view of an additional embodiment of the present invention in use with a blood collection set.

Alternatively, the safety shield assemblies of the present invention as described above may be used in conjunction with a conventional intravenous (IV) infusion set, as illustrated in FIG. 38.

For purposes of illustration, shield 140g and collar 90g are connected to a conventional IV infusion set 200 or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Figure 39:
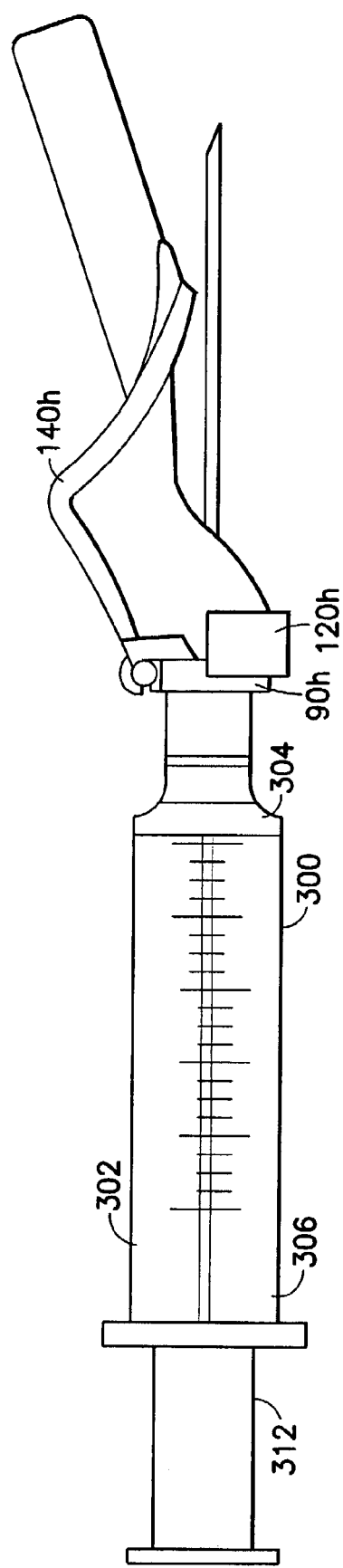
FIG. 39 is a perspective view of an additional embodiment of the present invention in use with a syringe.

Alternatively, the safety shield assemblies of the present invention as described above may be used in conjunction with a syringe, as illustrated in FIG. 39.

For purposes of illustration, shield 140h and collar 90h are connected to a conventional hypodermic syringe 300 comprising a syringe barrel 302 having a distal end 304, a proximal end 306 and a plunger 312.

Figure 40:
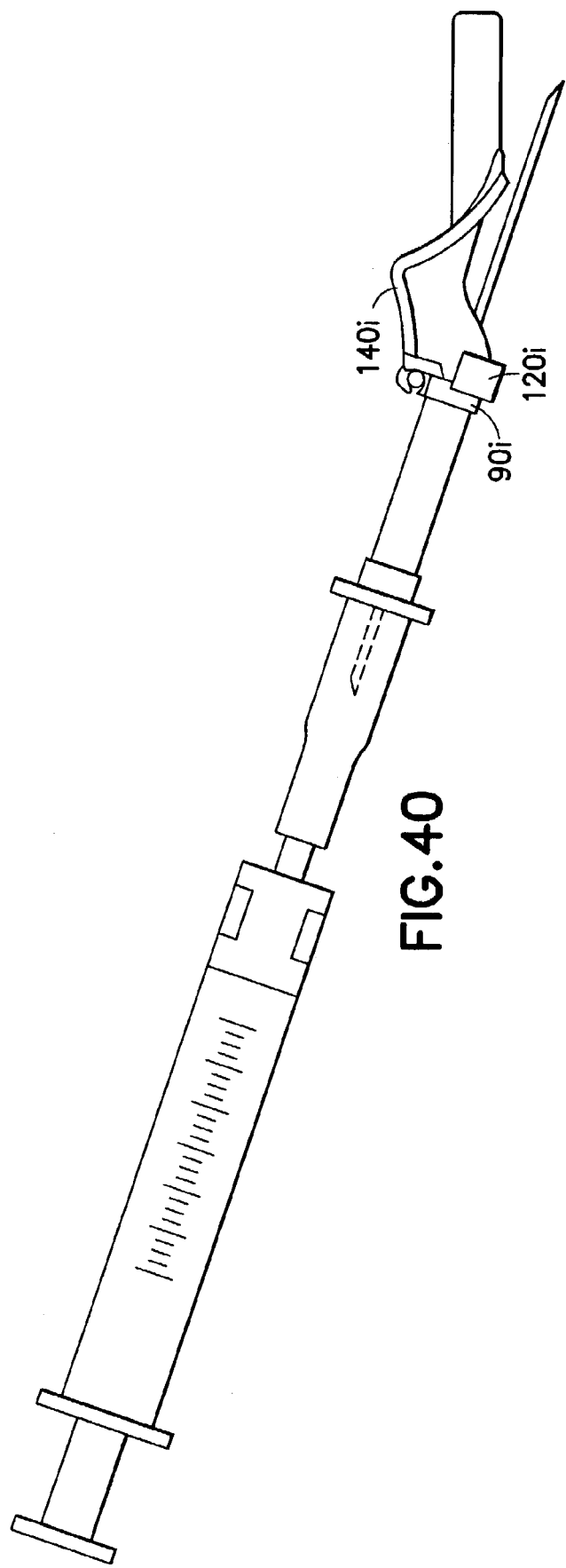
FIG. 40 is a perspective view of an additional embodiment of the present invention in use with a catheter.

Alternatively, the safety shield assemblies of the present invention as described above may be used in conjunction with a catheter, as illustrated in FIG. 40.

The shield and collar of the safety shield assembly of the present invention are comprised of moldable parts which can be mass produced from a variety of materials including, for example, polyethylene, polyvinyl chloride, polystyrene or polyethylene and the like. Materials will be selected which will provide the proper covering and support for the structure of the invention in its use, but which will provide also a degree of resiliency for the purpose of providing the cooperative movement relative to the shield and the collar of the assembly.

What is claimed is:

1. A safety needle assembly comprising:
   a needle cannula including an intravenous end having a puncture tip;
   a collar engaged with said needle cannula and including at least one collar flange extending laterally along a portion of said collar toward said intravenous end of said needle cannula in a forward direction generally parallel with an axis defined by the needle cannula; and
   a shield including a pair of longitudinally extending sidewalls defining a longitudinal opening, said shield pivotably connected to said collar and pivotal with respect to said needle cannula between an unshielded position pivotally spaced from said intravenous end of said needle cannula and a shielded position with said intravenous end of said needle cannula encompassed within said longitudinal opening,
   a first locking mechanism comprising at least one of said pair of sidewalls of said shield including a locking barb and said collar including a locking dent, said locking barb and said locking dent being interengagable when said shield is in said shielded position, thereby forming a first locking structure for preventing pivotal movement to said unshielded position,
   a second locking mechanism comprising, contact between said collar flange and said shield when said shield is in said shielded position, wherein said shield includes an outer shield flange on at least one of said pair of sidewalls, said outer shield flange and said at least one of said pair of sidewalls forming an opening for receiving said collar flange.

2. A safety needle assembly comprising:

a needle cannula including an intravenous end having a puncture tip;

a collar engaged with said needle cannula and including at least one collar flange extending laterally along a portion of said collar toward said intravenous end of said needle cannula in a forward direction generally parallel with an axis defined by the needle cannula; and a shield including a pair of longitudinally extending sidewalls defining a longitudinal opening, said shield pivotably connected to said collar and pivotal with respect to said needle cannula between an unshielded position pivotally spaced from said intravenous end of said needle cannula and a shielded position with said intravenous end of said needle cannula encompassed within said longitudinal opening, a first locking mechanism comprising at least one of said pair of sidewalls of said shield including a locking barb and said collar including a locking dent, said locking barb and said locking dent being interengagable when said shield is in said shielded position for preventing pivotal movement to said unshielded position, a second locking mechanism comprising an outer shield flange and an inner shield flange on at least one of said pair of sidewalls of said shield, and said collar flange, said outer shield flange and said inner shield flange forming an opening for receiving said collar flange when said shield is in said shielded position.

3. A safety needle assembly as in claim 2, wherein said outer shield flange is flexible.

4. A safety needle assembly as in claim 2, wherein said outer shield flange and said inner shield flange are interconnected.

5. A safety needle assembly as in claim 2, wherein said collar flange includes a rounded forward surface.

6. A safety needle assembly as in claim 2, wherein said outer shield flange and said inner shield flange form said locking structure for engagement with said collar flange.

7. A safety needle assembly as in claim 6, wherein said collar flange includes an outer latch for engagement with said outer shield flange.

8. A safety needle assembly as in claim 7, wherein said collar flange further includes an inner latch for engagement with said inner shield flange.

* * * * *